US006653448B1

(12) United States Patent
Vernet et al.

(10) Patent No.: US 6,653,448 B1
(45) Date of Patent: Nov. 25, 2003

(54) WNT-7B-LIKE POLYPEPTIDES AND NUCLEIC ACIDS ENCODING SAME

(75) Inventors: Corine Vernet, North Branford, CT (US); Luca Rastelli, Guilford, CT (US); John Herrmann, Gilford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/625,634

(22) Filed: Jul. 26, 2000

Related U.S. Application Data
(60) Provisional application No. 60/194,256, filed on Apr. 3, 2000, and provisional application No. 60/192,838, filed on Mar. 29, 2000.

(51) Int. Cl.[7] .............................................. C07K 14/00
(52) U.S. Cl. ...................................................... 530/350
(58) Field of Search ............................ 530/350; 514/12

(56) References Cited

U.S. PATENT DOCUMENTS

| 5,539,598 A | 7/1996 | Denison et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,916,771 A | 6/1999 | Hori et al. |

FOREIGN PATENT DOCUMENTS

| EP | 879886 A2 | * 11/1998 |
| EP | 0 887 408 A1 | 12/1998 |
| WO | WO 94/02602 | 2/1994 |
| WO | WO 9517416 A1 | * 6/1995 |
| WO | WO 96/33735 | 10/1996 |
| WO | WO 96/34096 | 10/1996 |
| WO | WO 98/06747 | 2/1998 |
| WO | WO 9929719 A2 | * 6/1999 |
| WO | WO 9946281 A2 | * 9/1999 |
| WO | WO 99/53049 | 10/1999 |
| WO | WO 9957248 A1 | * 11/1999 |
| WO | WO 99/57248 | 11/1999 |

OTHER PUBLICATIONS

Tockman, MS, et al, 1992, Considerations in bringing a cancer biomarker to clinical application, Cancer Research, vol. 52, Suppl., pp. 2711s–2718s.*
Gura, T, 1997, Systems for identifying drugs are often faulty, Science, vol. 278, pp. 1041–1042.*
De Plaen, E, et al, 1994, Structure, chromosomal localization, and expression of 12 genes of the MAGE family, Immunogenetics, vol. 40, pp. 360–369.*
Burgess, WH, et al, 1990, Possible dissociation of the heparin–binding and mitogenic activities of a heparin–binding (acidic fibroblast) growth factor–1, J Cell Biology, vol. 111, pp. 2129–2138.*
Lazar, E, et al, 1988, Transforming growth factor alpha: mutation of aspartic acid 47 and leucine 48 results in different biological activities, Molecular and Cellular Biology, vol. 8, pp. 1247–1252.**
Bodey, B, et al, 2000,Failure of cancer vaccines: the significant limitations of this approach to immunotherapy, Anticancer Research, vol. 20, pp. 2665–2676.*
Bork, P, 2000, Powers and pitfalls in sequence analysis: the 70% hurdle, Genome Research, vol. 10, pp. 398–400.*
Bergers, G, et al, 2000, Extrinsic regulators of epithelial tumor progression: metalloproteinases, Current Opinion in Genetics & Development, vol. 10, pp. 120–127.*
Caubit, X, et al, Submitted Nov. 1996, Database EMBL/GenBank/DDBJ, Accession No. O13266, WNT–7A, Pleurodeles waltlii (Iberian ribbed newt).*
International Search Report for PCT/US 01/10679, filed Apr. 3, 2001.
Chang, C. and Hemmati–Brivanlou, A. (1998), "Neural Crest Induction by Xwnt7B in Xenopus." *Developmental Biology* 194(1): 129–34.
EMBL Database Accession No.: AF026894 (1997).
Gavin, B.J. et al. (1990), "Expression of Multiple Novel Wnt–1/int–1–related Genes During Fetal and Adult Mouse Development."*Genes and Development* 4(12B): 2319–32.
Huguet, E.L. et al. (1994), "Differential Expression of Human Wnt Genes 2, 3, 4, and 7B in Human Breast Cell Lines and Normal and Disease States of Human Breast Tissue." *Cancer Research* 54(10): 2615–21.
Bui, T.D. et al. (1998), "High Expression of Wnt 7B in Human Superficial Bladder Cancer v. Invasive Bladder Cancer." *British J. of Cancer* 77(2): 319–24.
van Bokhoven, H. et al. (1997), "Assignment of Wnt 7B to Human Chromosome Band 22q13 by in situ Hybridization." *Cytogenetics and Cell Genetics* 77(3–4): 288–89.
Kirikoshi, H. et al. (2001), "Molecular Cloning and Characterization of Human Wnt 7B." *Int'l J. of Oncology* 19(4): 779–83.

(List continued on next page.)

*Primary Examiner*—Anthony C. Caputa
*Assistant Examiner*—Stephen L. Rawlings
(74) *Attorney, Agent, or Firm*—Mintz Levin Cohn Ferris Glovsky & Popeo, PC; Ivor R. Elrifi, Esq.; Cynthia A. Kozakiewicz, Esq.

(57) ABSTRACT

The present invention provides novel isolated Wnt-7B-like polynucleotides and the membrane-associated or secreted polypeptides encoded by the Wnt-7B-like polynucleotides. Also provided are the antibodies that immunospecifically bind to a Wnt-7B-like polypeptide or any derivative, variant, mutant or fragment of the Wnt-7B-like polypeptide, polynucleotide or antibody. The invention additionally provides methods in which the Wnt-7B-like polypeptide, polynucleotide and antibody are utilized in the detection and treatment of a broad range of pathological states, as well as to other uses.

2 Claims, 5 Drawing Sheets

OTHER PUBLICATIONS

Bui et al. (1998). "High expression of Wnt7b in human superficial bladder cancer vs invasive bladder cancer." *Br J Cancer* 77(2): 319–324.

Burrus and McMahon (1995). "Biochemical analysis of murine Wnt proteins reveals both shared and distinct properties." *Exp Cell Res* 220(2): 363–373.

Cote et al.(1983). "Generation of human monoclonal antibodies reactive with cellular antigens." *Proc. Natl. Acad. Sci. USA* 80: 2026–2030.

Fishwild et al. (1996). "High–avidity human IgG kappa monoclonal antibodies from a novel strain of minilocus transgenic mice." *Nat Biotechnol* 14(7): 845–851.

GenBank Accession No.: P28047 (Oct. 16, 2001).

Hoogenboom and Winter (1992). "By–passing immunisation. Human antibodies from synthetic repertoires of germ-line VH gene segments rearranged in vitro." *J Mol Biol* 227(2): 381–388.

Kozbor and Roder (1983). "The production of monoclonal antibodies from human lymphocytes." *Immunology Today* 4(3): 72–79.

Lonberg and Huszar (1995). "Human antibodies from transgenic mice." *Int Rev Immunol* 13(1): 65–93.

Lonberg et al. (1994). "Antigen–specific human antibodies from mice comprising four distinct genetic modifications." *Nature* 368(6474): 856–859.

Marks et al. (1992). "By–passing immunization: building high affinity human antibodies by chain shuffling." *Biotechnology (N Y)* 10(7): 779–783.

Marks et al. (1991). "By–passing immunization. Human antibodies from V–gene libraries displayed on phage." *J Mol Biol* 222(3): 581–597.

Morrison (1994). "Immunology. Success in specification." *Nature* 368(6474): 812–13.

Neuberger (1996). "Generating high–avidity human Mabs in mice." *Nat Biotechnol* 14(7): 826.

Nguyen et al. (1999). "Expression of the Wnt gene family during late nephrogenesis and complete ureteral obstruction." *Lab Invest* 79(6): 647–658.

Peifer and Polakis (2000). "Wnt signaling in oncogenesis and embryogenesis—a look outside the nucleus." *Science* 287(5458): 1606–1609.

SWALL (SPTR) Accession No.: Q9Y560 (Nov. 1, 1997).

Wong et al. (1994). "Differential transformation of mammary epithelial cells by Wnt genes." *Mol Cell Biol* 14(9): 6278–6286.

* cited by examiner

Figure 1. Nucleotide sequence including the sequence encoding the Wnt-7B-like protein of the invention.

```
ATGCACAGAAACTTTCGCAAGTGGATTTTCTACGTGTTTCTCTGCTTTGGCGTCCTGTACGTGAAGCTCGGA
GCACTGTCATCCGTGGTGGCCCTGGGAGCCAACATCATCTGCAACAAGATTCCTGGCCTAGCCCCGCGGCAG
CGTGCCATCTGCCAGAGTCGGCCCGATGCCATCATTGTGATTGGGGAGGGGCGCAGATGGGCATCAACGAG
TGCCAGTACCAGTTCCGCTTCGGACGCTGGAACTGCTCTGCCCTCGGCGAGAAGACCGTCTTCGGGCAAGAG
CTCCGAGTAGGGAGCCGTGAGGCTGCCTTCACGTACGCCATCACCGCGGCTGGCGTGGCGCACGCCGTCACC
GCTGCCTGCAGCCAAGGGAACCTGAGCAACTGCGGCTGCGACCGCGAGAAGCAGGGCTACTACAACCAAGCC
GAGGGCTGGAAGTGGGGCGGCTGCTCGGCCGACGTGCGTTACGGCATCGACTTCTCCCGGCGCTTCGTGGAC
GCTCGGGAGATCAAGAAGAACGCGCGGCGCCTCATGAACCTGCATAACAATGAGGCCGGCAGGAAGGTTCTA
GAGGACCGGATGCAGCTGGAGTGCAAGTGCCACGGCGTGTCTGGCTCCTGCACCACCAAAACCTGCTGGACC
ACGCTGCCCAAGTTCCGAGAGGTGGGCCACCTGCTGAAGGAGAAGTACAACGCGGCCGTGCAGGTGGAGGTG
GTGCGGGCCAGCCGTCTGCGGCAGCCCACCTTCCTGCGCATCAAACAGCTGCGCAGCTATCAGAAGCCCATG
GAGACAGACCTGGTGTACATTGAGAAGTCGCCCAACTACTGCGAGGAGGACGCGGCCACGGGCAGCGTGGGC
ACGCAGGGCCGTCTCTGCAACCGCACGTCGCCCGGCGCGGACGACTGTGACACCATGTGCTGCGGCCGAGGC
TACAACACCCACCAGTACACCAAGGTGTGGCAGTGCAACTGCAAATTCCACTGGTGCTGCTTCGTCAAGTGC
AACACCTGCAGCGAGCGCACCGAGGTCTTCACCTGCAAGTGAGCCAGGCCCGGAGGCGGCCC (SEQ ID
NO:1)
```

FIG 2A. Protein sequence encoded by the coding sequence shown in Figure 1.

MHRNFRKWIFYVFLCFGVLYVKLGALSSVVALGANIICNKIPGLAPRQRAICQSRPDAIIVIGEGAQMGINECQYQFRF
GRWNCSALGEKTVFGQELRVGSREAAFTYAITAAGVAHAVTAACSQGNLSNCGCDREKQGYYNQAEGWKWGGCSADVRY
GIDFSRRFVDAREIKKNARRLMNLHNNEAGRKVLEDRMQLECKCHGVSGSCTTKTCWTTLPKFREVGHLLKEKYNAAVQ
VEVVRASRLRQPTFLRIKQLRSYQKPMETDLVYIEKSPNYCEEDAATGSVGTQGRLCNRTSPGADDCDTMCCGRGYNTH
QYTKVWQCNCKFHWCCFVKCNTCSERTEVFTCK (SEQ ID NO:2)

FIG. 2B Amino acid sequence of a murine Wnt-7B-polypeptide

MHRNFRKWIFYVFLCFGVLYVKLGALSSVVALGANIICNKIPGLAPRQRAICQSRPDAIIVIGEGAQMGI
DECQHQFRFGRWNCSALGEKTVFGQELRVGSREAAFTYAITAAGVAHAVTAACSQGNLSNCGCDREKQGY
YNQAEGWKWGGCSADVRYGIDFSRRFVDAREIKKNARRLMNLHNNEAGRKVLEDRMKLECKCHGVSGSCT
TKTCWTTLPKFREVGHLLKEKYNAAVQVEVVRASRLRQPTFLRIKQLRSYQKPMETDLVYIEKSPNYCEE
DAATGSVGTQGRLCNRTSPGADGCDTMCCGRGYNTHQYTKVWQCNCKFHWCCFVKCNTCSERTEVFTCK
(SEQ ID NO:3)

WNT-7B-LIKE POLYPEPTIDES AND NUCLEIC ACIDS ENCODING SAME

RELATED APPLICATIONS

This application claims priority to U.S. Ser. No. 60/192,838, filed Mar. 29, 2000, and to U.S. Ser. No. 60/194,256, filed Apr. 3, 2000, which are incorporated herein by reference in their entireties.

FIELD OF THE INVENTION

The invention relates to nucleic acids and polypeptides.

BACKGROUND OF THE INVENTION

The Wnt gene family includes at least ten genes that encode structurally related secreted glycoproteins. Members of the Wnt family are reported to be regulators of mammary cell growth and differentiation. For example, members have been shown to control a variety of developmental processes, e.g., cell fate specification, cell proliferation, cell polarity and cell migration. In addition, dysregulation of Wnt signaling has been reported to cause developmental defects, and to be implicated in the genesis of several human cancers.

Wnt family gene members Wnt-4, -7b, and -11 are expressed in metanephric kidneys. The expression of members of the Wnt gene family has been examined during kidney formation and in processes associated with complete urethral obstruction. Urethral obstruction induced during metanephrogenesis disrupts the normal pattern of Wnt-7b expression and interferes with the normal transformation process in developing kidneys, by maintaining the mesenchymal component and inducing the transformation of epithelium to mesenchyme. Accordingly, Wnt proteins may serve as mediators of the transformation of renal mesenchyme to epithelium.

Overexpression of Wnt-7B proteins can result in cellular transformation of C57MG cells. Higher levels expression of Wnt7b has also been reported in superficial bladder cancer cells as compared to invasive bladder cancer. These results suggest the Wnt-7B protein is involved in the early events of bladder tumorigenesis.

SUMMARY OF THE INVENTION

The present invention is based, in part, upon the discovery of a novel human nucleic acid sequence encoding a polypeptide having sequence similarity to Wnt-7B. The Wnt-7B like nucleic acids, polynucleotides, proteins and polypeptides or fragments thereof described herein include those found in clone 29518614.0.61 (SEQ ID NO:1), and the polypeptide encoded by clone 29518614.0.61 (SEQ ID NO:2).

In one aspect, the invention includes an isolated Wnt-7B-like nucleic acid molecule which includes a nucleotide sequence encoding a polypeptide that includes the amino acid sequence of SEQ ID NO:2. For example, in various embodiments, the nucleic acid can include a nucleotide sequence that includes SEQ ID NO:1. Alternatively, the encoded Wnt-7B-like polypeptide may have a variant amino acid sequence, e.g., have an identity or similarity less than 100% to the disclosed amino acid sequences, as described herein.

The invention also includes an isolated polypeptide that includes the amino acid sequence of SEQ ID NO:2 or a fragment having at least 6 amino acids of these amino acid sequences. Also included is a naturally occurring polypeptide variant of a Wnt-7B-like polypeptide, wherein the polypeptide is encoded by a nucleic acid molecule which hybridizes under stringent conditions to a nucleic acid molecule consisting of a Wnt-7B-like nucleic acid molecule.

Also included in the invention is an antibody that selectively binds to a Wnt-7B-like polypeptide. The antibody is preferably a monoclonal antibody, and most preferably is a human antibody. Such antibodies are useful, for example, in the treatment of a pathological state in a subject wherein the treatment includes administering the antibody to the subject.

The invention further includes a method for producing a Wnt-7B-like polypeptide by culturing a host cell expressing one of the herein described Wnt-7B-like nucleic acids under conditions in which the nucleic acid molecule is expressed.

The invention also includes methods for detecting the presence of a Wnt-7B-like polypeptide or nucleic acid in a sample from a mammal, e.g., a human, by contacting a sample from the mammal with an antibody which selectively binds to one of the herein described polypeptides, and detecting the formation of reaction complexes including the antibody and the polypeptide in the sample. Detecting the formation of complexes in the sample indicates the presence of the polypeptide in the sample.

The invention further includes a method for detecting or diagnosing the presence of a disease, e.g., a pathological condition, associated with altered levels of a polypeptide having an amino acid sequence at least 80% identical to a Wnt-7B-like polypeptide in a sample. The method includes measuring the level of the polypeptide in a biological sample from the mammalian subject, e.g., a human, and comparing the level detected to a level of the polypeptide present in normal subjects, or in the same subject at a different time, e.g., prior to onset of a condition. An increase or decrease in the level of the polypeptide as compared to normal levels indicates a disease condition.

Also included in the invention is a method of detecting the presence of a Wnt-7B-like nucleic acid molecule in a sample from a mammal, e.g., a human. The method includes contacting the sample with a nucleic acid probe or primer which selectively hybridizes to the nucleic acid molecule and determining whether the nucleic acid probe or primer binds to a nucleic acid molecule in the sample. Binding of the nucleic acid probe or primer indicates the nucleic acid molecule is present in the sample.

The invention further includes a method for detecting or diagnosing the presence of a disease associated with altered levels of a Wnt-7B-like nucleic acid in a sample from a mammal, e.g., a human. The method includes measuring the level of the nucleic acid in a biological sample from the mammalian subject and comparing the level detected to a level of the nucleic acid present in normal subjects, or in the same subject at a different time. An increase or decrease in the level of the nucleic acid as compared to normal levels indicates a disease condition.

The invention also includes a method of treating a pathological state in a mammal, e.g., a human, by administering to the subject a Wnt-7B-like polypeptide to the subject in an amount sufficient to alleviate the pathological condition. The polypeptide has an amino acid sequence at least 80% identical to a Wnt-7B-like polypeptide.

Alternatively, the mammal may be treated by administering an antibody as herein described in an amount sufficient to alleviate the pathological condition.

Pathological states for which the methods of treatment of the invention are envisioned include a cancer, e.g., colorectal carcinoma, a prostate cancer benign tumor, an immune disorder, an immune deficiency, an autoimmune disease, acquired immune deficiency syndrome, transplant rejection, allergy, an infection by a pathological organism or agent, an inflammatory disorder, arthritis, a hematopoietic disorder, a skin disorder, atherosclerosis, restenosis, a neurological disease, Alzheimer's disease, trauma, a surgical or traumatic wound, a spinal cord injury, and a skeletal disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a representation of a Wnt-7B-1 nucleotide sequence (SEQ ID NO:1) according to the invention.

FIG. 2A is a representation of a Wnt-7B-1 polypeptide sequence (SEQ ID NO:2) according to the invention.

FIG. 2B is a representation of a murine Wnt-7B polypeptide sequence (SEQ ID NO:3).

DETAILED DESCRIPTION OF THE INVENTION

Figure 3A:
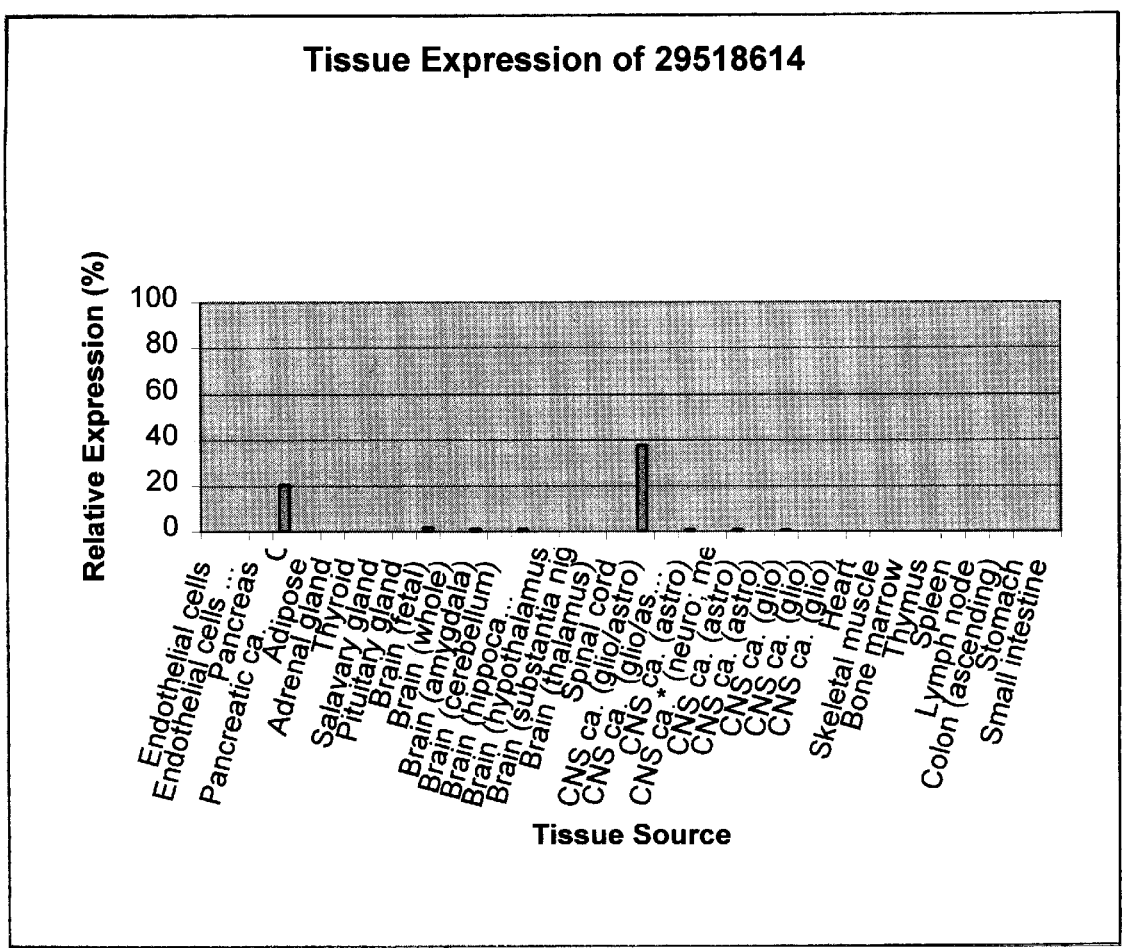
FIGS. 3A–3C are representations of expression analyses of a Wnt-7B-1 nucleic acid according to the invention.

The invention provides Wnt-7B-1 like nucleic acids, and polypeptides encoded by these nucleic acids. Included in the invention is a novel nucleic acid of 1072 nucleotides (SEQ ID NO:1), which is also referred to herein as clone 29518614.0.61. This sequence is shown in FIG. 1.

An open reading frame in SEQ ID NO:1 was identified beginning with an ATG initiation codon at nucleotides 1–3 and ending with a TGA codon at nucleotides 1048–1050. The amino acid sequence of the encoded protein is 349 amino acid residues and is presented in FIG. 2A.

The encoded protein has 345 of 349 amino acid (98%) identity to Mus musculus Wnt-7B protein (ACC:P28047) (FIG. 2B). The full amino acid sequence of the protein has 268 of 349 amino acid residues (76%) identical to, and 316 of 349 residues (90%) positive with, the 349 amino acid residue Wnt7A protein from *Homo sapiens* (ptnr:SPTREMBL-ACC: Q9Y560).

PSORT analysis predicts the encoded protein to be localized in the plasma membrane, with a certainty of 0.6850. Using the SIGNALP analysis, it is predicted that the protein of the invention has a non-cleavable amino terminal signal sequence with a most likely cleavage site between pos. 31 and 32: VVA-LG. The predicted molecular weight of the protein of the invention is 39384.8 daltons.

The nucleic acids and proteins of the invention are useful in, e.g., therapeutic applications implicated in (a) developmental diseases, including those related to nephrogenesis; (b) tumorigenesis and cancer, including breast cancer and bladder cancer; and (c) other pathologies and disorders.

For example, a cDNA encoding the Wnt-7B-like protein may be useful in Wnt-7B therapy, and the Wnt-7B-like protein may be useful when administered to a subject in need thereof. By way of nonlimiting example, the compositions of the present invention will have efficacy for treatment of patients suffering from developmental diseases, cancer, and/or other pathologies and disorders. The novel nucleic acid encoding Wnt-7B-like protein, and the Wnt-7B-like protein of the invention, or fragments thereof, may further be useful in diagnostic applications, wherein the presence or amount of the nucleic acid or the protein are to be assessed. These materials are further useful in the Wnt-7B ration of antibodies that bind immunospecifically to the novel substances of the invention for use in therapeutic or diagnostic methods.

Wnt-7B-like nucleic acids of the invention show high expression in multiple tumor cell lines from all major carcinoma groups. Accordingly, the Wnt-7B-like polypeptides according to the invention may have a role in autocrine stimulation of tumor growth, chemoresistance, radiotherapy resistance, survival to loss of adhesion therefore role in stimulating tumor cell migration (invasion). Based on the roles of related molecules in cell adhesion and migration and the gene expression profile, it is anticipated that for many tumor types, successful targeting of a Wnt-7B-like polypeptide, e.g., a polypeptide having the amino acid sequence of SEQ ID NO:2, using a monoclonal antibody will have an inhibitory effect on tumor growth.

Polynucleotides and polypeptides disclosed herein are shown in Table 1, along with their corresponding sequence identifier numbers.

TABLE 1

Sequences and Corresponding SEQ ID Numbers

| Clone or Primer No. | SEQ ID Number |
|---|---|
| Wnt-7B-like nucleic acid molecule (clone 29518614.0.61) | 1 |
| Polypeptide encoded by clone 29518614.0.61 | 2 |
| Murine Wnt-7B polypeptide | 3 |
|  | 4 |
| Ag 316 (R) | 5 |
| Ag 316 (P): | 6 |

Wnt-7B-Like Nucleic Acids

Provided by the invention is an isolated nucleic acid molecule (e.g., SEQ ID NO:1) that encodes a Wnt-7B-like polypeptide. In some embodiments, the nucleic acid molecule encodes a Wnt-7B-like polypeptide including the amino acid sequence of SEQ IQ NO:2 (FIG. 2), or a biologically active portion thereof. The invention also includes nucleic acid fragments sufficient for use as hybridization probes to identify Wnt-7B-like-encoding nucleic acids (e.g., Wnt-7B-like mRNA) and fragments for use as PCR primers for the amplification or mutation of Wnt-7B-like nucleic acid molecules. As used herein, the term "polynucleotide" or "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA. Wnt-7B-like nucleic acids of the invention include SEQ ID NO:1, and fragments, homologs, and derivatives thereof.

In another embodiment the nucleic acid molecule encodes a Wnt-7B-like polypeptide that includes an amino acid sequence other than IDE at positions 70–72, QHQ at positions 74–76, MKL at positions 196–198, or DGC at positions 302–304. For example, the isolated nucleic acid can encode a polypeptide that includes at least one of the amino acid sequences INE at positions 70–72, QYQ at positions 74–76, MQL at positions 196–198, and DDC at positions 302–304. In some embodiments, the nucleic acid molecule encodes a polypeptide having two or three of these tripeptide sequences.

"Probes" refer to nucleic acid sequences of variable length, preferably between at least about 10 nucleotides (nt), 100 nt, or as many as about, e.g, 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, an isolated nucleic acid molecule encoding a Wnt-7B-like polypeptides, such as the Wnt-7B-like protein of the invention can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., adult and fetal cells from tissues including bone tissue (including bone marrow), heart, lymph node, pancreas, spleen, thymus, placenta, kidney, liver, thalamus, brain, pituitary, breast, lung, salivary gland and adrenal gland). Moreover, an "isolated" nucleic acid molecule, e.g., a cDNA molecule, can be substantially free of other cellular material or culture medium when produced by recombinant techniques, or of chemical precursors or other chemicals when chemically synthesized.

A nucleic acid molecule of the present invention, e.g., a Wnt-7B-like nucleic acid molecule having the nucleotide sequence of SEQ ID NO:1, or a complement of any of these nucleotide sequences, can be isolated using standard molecular biology techniques and the sequence information provided herein. Using all or a portion of the Wnt-7B-like nucleic acid sequences of SEQ ID NO:1, or a complement of any of these nucleotide sequences, as a hybridization probe, said Wnt-7B-like molecules can be isolated using standard hybridization and cloning techniques (e.g., as described in Sambrook et al., (eds.), *MOLECULAR CLONING: A LABORATORY MANUAL* 2*nd* Ed., Cold Spring Harbor Laboratory Press, Cold Spring Harbor, N.Y., 1989; and Ausubel, et al., (eds.), *CURRENT PROTOCOLS IN MOLECULAR BIOLOGY*, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore; oligonucleotides corresponding to Wnt-7B-like nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nucleotides in length, preferably about 15 nucleotides to 30 nucleotides in length. In one embodiment, an oligonucleotide comprising a nucleic acid molecule less than 100 nucleotides in length would further comprise at lease 6 contiguous nucleotides of SEQ ID NO:1, or a complement thereof. Oligonucleotides may be chemically synthesized and may be used as probes.

In an embodiment, an isolated nucleic acid molecule of the invention comprises a Wnt-7B-like nucleic acid molecule that is a complement of the nucleotide sequence shown in SEQ ID NO:1, or a portion of this nucleotide sequence. A nucleic acid molecule that is complementary to said Wnt-7B-like nucleotide sequences is one that is sufficiently complementary to the nucleotide sequence shown in SEQ ID NO:1, or a portion of this nucleotide sequence, that it can hydrogen bond with little or no mismatches to the given Wnt-7B-like nucleotide sequence, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, or the nucleotide sequence of the DNA insert of the plasmid, e.g., e.g., the pSecTag2 B and pSecV5His vectors described in Example 3, wherein e.g., a fragment that can be used as a probe or primer or a fragment encoding a biologically active portion of Wnt-7B-like. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially similar to the nucleic acids or proteins of the invention, in various embodiments, by at least about 30%, 50%, 70%, 80%, 95%, 98%, or 99% identity (with a preferred identity of 80–95%) over a nucleic acid or amino acid sequence of identical size or when compared to an aligned sequence in which the alignment is done by a computer similarity program known in the art (e.g., see below), or whose encoding nucleic acid is capable of hybridizing to the complement of a sequence encoding the aforementioned proteins under stringent, moderately stringent, or low stringent conditions. See e.g. Ausubel, et al., *CURRENT PROTOCOLS IN MOLECULAR BIOLOGY*, John Wiley & Sons, New York, N.Y., 1993, and below.

In some embodiments, the nucleic acid encoding a Wnt-7B derivative or analog differs by the above-percentages from SEQ ID NO:2 and encode an amino acid sequence other than IDE at positions 70–72, QHQ at positions 74–76, MKL at positions 196–198, or DGC at positions 302–304. For example, the isolated nucleic acid can encode a polypeptide that includes at least one of the amino acid sequences INE at positions 70–72, QYQ at positions 74–76, MQL at positions 196–198, and DDC at positions 302–304. In some embodiments, the nucleic acid molecule encodes a polypeptide having two or three of these tri-peptide sequences.

A "homologous nucleic acid sequence", "homologous amino acid sequence," "similar nucleic acid sequence" or "similar amino acid sequence", or variations of these phrases, refer to sequences characterized by a homology or similarity at the nucleotide level or amino acid level, respectively, as discussed above. Similar nucleotide sequences encode amino acid sequences that are isoforms, variants, paralogs or orthologs of the Wnt-7B-like polypeptide of the invention. Isoforms can be expressed in different tissues of the same organism as a result of, for example, alternative splicing of RNA. Alternatively, isoforms can be encoded by different genes. In the present invention, similar nucleotide sequences include nucleotide sequences encoding a Wnt-7B-like polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A similar nucleotide sequence does not, however, include the nucleotide sequence encoding human or murine Wnt-7B-like protein. Similar nucleic acid sequences include those nucleic acid sequences that encode conservative amino acid substitutions (see below) in SEQ ID NO:2, as well as a polypeptide having Wnt-7B-like activity. Biological activities of the individual Wnt-7B-like proteins are described above. A similar amino acid sequence does not encode the amino acid sequence of a human or murine Wnt-7B-like polypeptide.

A Wnt-7B-like polypeptide is encoded by the open reading frame ("ORF") of a Wnt-7B-like nucleic acid. The invention includes the nucleic acid sequence comprising the stretch of nucleic acid sequences of SEQ ID NO:1, that comprises the ORF of that nucleic acid sequence and encodes a polypeptide of SEQ ID NO:2.

An "open reading frame" ("ORF") corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, for example, a stretch of DNA that would encode a protein of 50 amino acids or more.

The nucleotide sequence determined from the cloning of the human Wnt-7B-like gene allows for the generation of probes and primers designed for use in identifying and/or cloning Wnt-7B-like homologues, such as isoforms and paralogs, in other cell types, e.g. from other tissues, as well as Wnt-7B-like homologues, such as orthologs, from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO:1, or the nucleotide sequence of the DNA insert of the plasmid such as, e.g., the pSecTag2 B and pSecV5His vectors described in Example 3; or an anti-sense strand nucleotide sequence of a Wnt-7B-like nucleotide or the anti-sense strand Wnt-7B-like nucleotide sequence of the DNA insert of the plasmid known in the art; or of a naturally occurring mutant of a Wnt-7B-like nucleotide, or the naturally occurring mutant of the DNA insert of the plasmid vector known in the art.

Probes based on the human Wnt-7B-like nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a Wnt-7B-like protein, e.g., by measuring a level of a Wnt-7B-like-encoding nucleic acid in a sample of cells from a subject e.g., detecting Wnt-7B-like mRNA levels or determining whether a genomic Wnt-7B-like gene has been mutated or deleted.

"A polypeptide having a biologically active portion of Wnt-7B-like" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of Wnt-7B-like" can be prepared by isolating a portion of a Wnt-7B-like nucleotide that encodes a polypeptide having a Wnt-7B-like biological activity (wherein the biological activities of the Wnt-7B-like proteins are described above), expressing the encoded portion of Wnt-7B-like protein (e.g., by recombinant expression in vitro) and assessing the activity of the encoded portion of Wnt-7B-like. For example, a nucleic acid fragment encoding a biologically active portion of Wnt-7B-like may include an extracellular domain.

Wnt-7B-like Variant Nucleic Acids

The invention further encompasses a nucleic acid molecule that differs from the Wnt-7B-like nucleotide sequence shown in at least one of SEQ ID NO:1, due to degeneracy of the genetic code and thus encode the same Wnt-7B-like protein as that encoded by any of the above nucleotide sequences. In another embodiment, an isolated Wnt-7B-like nucleic acid molecule of the invention has a nucleotide sequence encoding a protein having the amino acid sequence shown in SEQ ID NO:2.

In addition to these human Wnt-7B-like nucleotide sequences, or the Wnt-7B-like nucleotide sequence of the DNA insert of a plasmid or vector, it will be appreciated by those skilled in the art that DNA sequence polymorphisms that lead to changes in the amino acid sequences of a Wnt-7B-like may exist within a population (e.g., the human population). Such genetic polymorphism in a Wnt-7B-like gene may exist among individuals within a population due to natural allelic variation. As used herein, the terms "gene" and "recombinant gene" refer to nucleic acid molecules comprising an open reading frame encoding a Wnt-7B-like protein, preferably a mammalian Wnt-7B-like protein. Such natural allelic variations can typically result in 1–5% variance in the nucleotide sequence of the Wnt-7B-like gene. Any and all such nucleotide variations and resulting amino acid polymorphisms in Wnt-7B-like that are the result of natural allelic variation and that do not alter the functional activity of Wnt-7B-like are intended to be within the scope of the invention.

Moreover, nucleic acid molecules encoding Wnt-7B-like proteins from other species, and thus that have a nucleotide sequence that differs from the human sequence disclosed herein, are intended to be within the scope of the invention. Nucleic acid molecules corresponding to natural allelic variants and homologues of a Wnt-7B-like cDNAs of the invention can be isolated based on their similarity to the human Wnt-7B-like nucleic acids disclosed herein using the human cDNAs, or a portion thereof, as a hybridization probe according to standard hybridization techniques under stringent hybridization conditions. For example, a soluble human Wnt-7B-like cDNA can be isolated based on its similarity to human membrane-bound Wnt-7B-like. Likewise, a membrane-bound human Wnt-7B-like cDNA can be isolated based on its similarity to soluble human Wnt-7B-like.

Accordingly, in another embodiment, an isolated nucleic acid molecule of the invention is at least 6 nucleotides in length and hybridizes under stringent conditions to the nucleic acid molecule comprising at least one Wnt-7B-like nucleotide sequence. In another embodiment, the nucleic acid is at least 10, 25, 50, 100, 250, 500 or 2000 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% similar to each other typically remain hybridized to each other.

Orthologs (i.e., nucleic acids encoding Wnt-7B-like proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), *CURRENT PROTOCOLS IN MOLECULAR BIOLOGY*, John Wiley & Sons, N.Y. (1989), 6.3.1–6.3.6. Preferably, the conditions are such that sequences at least about 65%, 70%, 75%, 85%, 90%, 95%, 98%, or 99% similar to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to a Wnt-7B-like nucleotide sequence corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to at least one Wnt-7B-like nucleic acid molecule, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known in the art. See, e.g., Ausubel et al. (eds.), 1993, *CURRENT PROTOCOLS IN MOLECULAR BIOLOGY*, John Wiley & Sons, NY, and Kriegler, 1990, *GENE TRANSFER AND EXPRESSION, A LABORATORY MANUAL*, Stockton Press, NY.

In a third embodiment, a nucleic acid that is hybridizable to at least one Wnt-7B-like nucleic acid molecule, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g. Ausubel et al. (eds.), 1993, *CURRENT PROTOCOLS IN MOLECULAR BIOLOGY*, John Wiley & Sons, NY, and Kriegler, 1990, *GENE TRANSFER AND EXPRESSION, A LABORATORY MANUAL*, Stockton Press, NY; Shilo and Weinberg, 1981, *Proc Natl Acad Sci USA* 78: 6789–6792.

Conservative Mutations

In addition to naturally-occurring allelic variants of the Wnt-7B-like sequence that may exist in the population, the skilled artisan will further appreciate that changes can be introduced by mutation into at least one Wnt-7B-like nucleotide sequence of SEQ ID NO:1, thereby leading to changes in the amino acid sequence of the encoded Wnt-7B-like protein, without altering the functional ability of the Wnt-7B-like protein. For example, nucleotide substitutions leading to amino acid substitutions at "non-essential" amino acid residues can be made in the sequence of SEQ ID NO:2, or the Wnt-7B-like nucleotide sequence of the DNA insert of the plasmid or vector known in the art. A "non-essential" amino acid residue is a residue that can be altered from the wild-type sequence of Wnt-7B-like without altering the biological activity, whereas an "essential" amino acid residue is required for biological activity. For example, amino acid residues that are conserved among the Wnt-7B-like proteins of the present invention, are predicted to be particularly unamenable to alteration.

Another aspect of the invention pertains to nucleic acid molecules encoding Wnt-7B-like proteins that contain changes in amino acid residues that are not essential for activity. Such Wnt-7B-like proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 45% similar to at least one Wnt-7B-like amino acid sequence. Preferably, the protein encoded by the nucleic acid molecule is at least about 60% similar to at least one Wnt-7B-like polypeptide, more preferably at least about 70% similar, at least about 80% similar, at least about 90% similar, and most preferably at least about 95% similar to that given Wnt-7B-like polypeptide.

An isolated nucleic acid molecule encoding a Wnt-7B-like protein similar to a given Wnt-7B-like protein can be created by introducing one or more nucleotide substitutions, additions or deletions into the corresponding Wnt-7B-like nucleotide sequence, such that one or more amino acid substitutions, additions or deletions are introduced into the encoded protein.

Mutations can be introduced into SEQ ID NO:2, by standard techniques, e.g., site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Wnt-7B-like is replaced with another amino acid residue from the same side chain family. Alternatively, in another embodiment, mutations can be introduced randomly along all or part of a Wnt-7B-like coding sequence, e.g., by saturation mutagenesis, and the resultant mutants can be screened for Wnt-7B-like biological activity to identify mutants that retain activity. Following mutagenesis, the encoded Wnt-7B-like protein can be expressed by any recombinant technology known in the art and the activity of the protein can be determined.

In one embodiment, a mutant Wnt-7B-like protein can be assayed for (1) the ability to form protein:protein interactions with other Wnt-7B-like proteins, other cell-surface proteins, or biologically active portions thereof, (2) complex formation between a mutant Wnt-7B-like protein and a Wnt-7B-like ligand; (3) the ability of a mutant Wnt-7B-like protein to bind to an intracellular target protein or biologically active portion thereof; (e.g. avidin proteins).

Antisense

Another aspect of the invention pertains to isolated antisense nucleic acid molecules that are hybridizable to or complementary to a Wnt-7B-like nucleic acid molecule, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire Wnt-7B-like coding strand, or to only a portion thereof. Nucleic acid molecules encoding fragments, homologs, derivatives and analogs of a Wnt-7B-like protein, or antisense nucleic acids complementary to a Wnt-7B-like nucleic acid sequence, are additionally provided.

In one embodiment, an antisense nucleic acid molecule is antisense to a "coding region" of the coding strand of a nucleotide sequence encoding Wnt-7B-like. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding Wnt-7B-like. The term "noncoding region" refers to 5' and 3' sequences which flank the coding region that are not translated into amino acids (i.e., also referred to as 5' and 3' untranslated regions).

Given the coding strand sequences encoding Wnt-7B-like disclosed herein (e.g., SEQ ID NO:1), antisense nucleic acids of the invention can be designed according to the rules of Watson and Crick or Hoogsteen base pairing. The antisense nucleic acid molecule can be complementary to the entire coding region of Wnt-7B-like mRNA, but more preferably is an oligonucleotide that is antisense to only a portion of the coding or noncoding region of Wnt-7B-like mRNA. For example, the antisense oligonucleotide can be complementary to the region surrounding the translation start site of Wnt-7B-like mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Wnt-7B-like protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2' -o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Ribozymes and PNA Moieties

Nucleic acid modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, e.g., an mRNA to which they have a complementary region. Thus, ribozymes (e.g., hammerhead ribozymes (described in Haselhoff and Gerlach (1988) *Nature* 334:585–591)) can be used to catalytically cleave Wnt-7B-like mRNA transcripts to thereby inhibit translation of Wnt-7B-like mRNA. A ribozyme having specificity for a Wnt-7B-like-encoding nucleic acid can be designed based upon the nucleotide sequence of a Wnt-7B-like cDNA disclosed herein (i.e., SEQ ID NO:1). For example, a derivative of a Tetrahymena L-19IVS RNA can be constructed in which the nucleotide sequence of the active site is complementary to the nucleotide sequence to be cleaved in a Wnt-7B-like-encoding mRNA. See, e.g., Cech et al. U.S. Pat. No. 4,987,071; and Cech et al. U.S. Pat. No. 5,116,742. Alternatively, Wnt-7B-like mRNA can be used to select a catalytic RNA having a specific ribonuclease activity from a pool of RNA molecules. See, e.g., Bartel et al., (1993) *Science* 261:1411–1418.

Alternatively, Wnt-7B-like gene expression can be inhibited by targeting nucleotide sequences complementary to the regulatory region of a Wnt-7B-like gene (e.g., the Wnt-7B-like promoter and/or enhancers) to form triple helical structures that prevent transcription of the Wnt-7B-like gene in target cells. See generally, Helene. (1991) *Anticancer Drug Des.* 6: 569–84; Helene. et al. (1992) *Ann. N. Y Acad. Sci.* 660:27–36; and Maher (1992) *Bioassays* 14: 807–15.

In various embodiments, the nucleic acids of Wnt-7B-like can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids " or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of Wnt-7B-like can be used in therapeutic and diagnostic applications. For example, PNAs can be used as antisense or antigene agents for sequence-specific modulation of gene expression by, e.g., inducing transcription or translation arrest or inhibiting replication. PNAs of Wnt-7B-like can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of Wnt-7B-like can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of Wnt-7B-like can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity.

PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5' -(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A*. 86:6553–6556; Lemaitre et al., 1987, *Proc. Natl. Acad. Sci*. 84:648–652; PCT Publication No. W088/09810) or the blood-brain barrier (see, e.g., PCT Publication No. W089/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res*. 5:539–549). To this end, the oligonucleotide may be conjugated to another molecule, e.g., a peptide, a hybridization triggered cross-linking agent, a transport agent, a hybridization-triggered cleavage agent, etc.

Wnt-7B-like Proteins

The invention also provides a Wnt-7B-like protein. For example, the invention includes a polypeptide that includes an amino acid sequence other than IDE at positions 70–72, QHQ at positions 74–76, MKL at positions 196–198, or DGC at positions 302–304, with respect to the amino acid sequence of SEQ ID NO:2. For example, the isolated nucleic acid can encode a polypeptide that includes at least one of the amino acid sequences INE at positions 70–72, QYQ at positions 74–76, MQL at positions 196–198, and DDC at positions 302–304. In some embodiments, the polypeptide includes two or three of these tri-peptide sequences.

In some embodiments, the Wnt-7B-like protein includes a polypeptide that includes the amino acid sequence is provided in FIG. 2 (SEQ ID NO:2). The invention also includes a mutant or variant protein, any of whose residues may be changed from the corresponding residue shown in FIG. 2 while still encoding a protein that maintains its Wnt-7B-like activities and physiological functions, or a functional fragment thereof. In the mutant or variant protein, up to 20% or more of the residues may be so changed. In some embodiments, 1%, 2%, 3%, 5%, 7%, 9%, 10%, 13%, 15% of the residues are changed.

Also included in the invention is a polypeptide that is at least 80% homologous, e.g., 85%, 90%, 92%, 95%, 97%, 98%, or 99% homologous, to the amino acid sequence of SEQ ID NO:2, provided that the amino acid sequence of the polypeptide includes an amino acid sequence other than IDE at positions 70–72, QHQ at positions 74–76, MKL at positions 196–198, or DGC at positions 302–304, with respect to the amino acid sequence of SEQ ID NO:2. For example, the polypeptide can include at least one of the amino acid sequences INE at positions 70–72, QYQ at positions 74–76, MQL at positions 196–198, and DDC at positions 302–304. In some embodiments, the polypeptide includes two, three or four, of these tri-peptide sequences.

In general, an Wnt-7B-like variant that preserves Wnt-7B-like-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated Wnt-7B-like proteins, and biologically active portions thereof, or derivatives, fragments, analogs or homologs thereof. Also provided are polypeptide fragments suitable for use as immunogens to raise anti-Wnt-7B-like antibodies. In one embodiment, native Wnt-7B-like proteins can be isolated from cells or tissue sources by an appropriate purification scheme using standard protein purification techniques. In another embodiment, Wnt-7B-like proteins are produced by recombinant DNA techniques. Alternative to recombinant expression, a Wnt-7B-like protein or polypeptide can be synthesized chemically using standard peptide synthesis techniques.

An "isolated" or "purified" protein or biologically active portion thereof is substantially free of cellular material or other contaminating proteins from the cell or tissue source from which the Wnt-7B-like protein is derived, or substantially free from chemical precursors or other chemicals when chemically synthesized. The language "substantially free of cellular material" includes preparations of Wnt-7B-like protein in which the protein is separated from cellular components of the cells from which it is isolated or recombinantly produced. In one embodiment, the language "substantially free of cellular material" includes preparations of Wnt-7B-like protein having less than about 30% (by dry weight) of non-Wnt-7B-like protein (also referred to herein as a "contaminating protein"), more preferably less than about 20% of non-Wnt-7B-like protein, still more preferably less than about 10% of non-Wnt-7B-like protein, and most preferably less than about 5% non-Wnt-7B-like protein. When the Wnt-7B-like protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Wnt-7B-like protein in which the protein is separated from chemical precursors or other chemicals that are involved in the synthesis of the protein. In one embodiment, the language "substantially free of chemical precursors or other chemicals" includes preparations of Wnt-7B-like protein having less than about 30% (by dry weight) of chemical precursors or non-Wnt-7B-like chemicals, more preferably less than about 20% chemical precursors or non-Wnt-7B-like chemicals, still more preferably less than about 10% chemical precursors or non-Wnt-7B-like chemicals, and most preferably less than about 5% chemical precursors or non-Wnt-7B-like chemicals.

Biologically active portions of a Wnt-7B-like protein include peptides comprising amino acid sequences sufficiently similar to or derived from the amino acid sequence of the Wnt-7B-like protein, e.g., the amino acid sequence shown in SEQ ID NO:2, that include fewer amino acids than the full length Wnt-7B-like proteins, and exhibit at least one activity of a Wnt-7B-like protein. Typically, biologically active portions comprise a domain or motif with at least one activity of the Wnt-7B-like protein. A biologically active portion of a Wnt-7B-like protein can be a polypeptide which is, for example, 10, 25, 50, 100 or more amino acids in length.

A biologically active portion of a Wnt-7B-like protein of the invention may contain at least one structural domain of a Wnt-7B-like polypeptide. An alternative biologically active portion of a Wnt-7B-like protein may contain an extracellular domain of the Wnt-7B-like protein. Another biologically active portion of a Wnt-7B-like protein may contain the transmembrane domain of the Wnt-7B-like protein. Yet another biologically active portion of a Wnt-7B-like protein of the present invention may contain the intracellular domain of the Wnt-7B-like protein.

Moreover, other biologically active portions, in which other regions of the protein are deleted, can be prepared by recombinant techniques and evaluated for one or more of the functional activities of a native Wnt-7B-like protein.

In one embodiment, the Wnt-7B-like protein has the amino acid sequence shown in SEQ ID NO:2. In other embodiments, the Wnt-7B-like protein is substantially similar to SEQ ID NO:2, and retains the functional activity of that given Wnt-7B-like protein yet differs in amino acid sequence due to natural allelic variation or mutagenesis. For example, the polypeptide includes an amino acid sequence other than IDE at positions 70–72, QHQ at positions 74–76, MKL at positions 196–198, or DGC at positions 302–304. Accordingly, in another embodiment, the Wnt-7B-like protein is a protein that comprises an amino acid sequence at least about 75% similar to the amino acid sequence of SEQ ID NO:2, and retains the functional activity of the Wnt-7B-like protein.

This invention further features isolated Wnt-7B-like protein, or derivatives, fragments, analogs or homologs thereof, that is encoded by a nucleic acid molecule having a nucleotide sequence that hybridizes under stringent hybridization conditions to a nucleic acid molecule comprising the nucleotide sequence of SEQ ID NO:1.

Determining Similarity Between Two or More Sequences

To determine the percent similarity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are similar or identical at that position (i.e., as used herein amino acid or nucleic acid "similarity" is equivalent to amino acid or nucleic acid "identity").

The nucleic acid sequence similarity may be determined as the degree of identity between two sequences. The similarity may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (i.e., encoding) part of the DNA sequence shown in SEQ ID NO:1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. Similar calculation are used when comparing amino acid residues in polypeptide sequences.

Chimeric and Fusion Proteins

The invention also provides Wnt-7B-like chimeric or fusion proteins. As used herein, a Wnt-7B-like "chimeric protein" or "fusion protein" comprises a Wnt-7B-like polypeptide operatively linked to a non-Wnt-7B-like polypeptide. A "Wnt-7B-like polypeptide" refers to a polypeptide having an amino acid sequence corresponding to Wnt-7B-like, whereas a "non-Wnt-7B-like polypeptide" refers to a polypeptide having an amino acid sequence corresponding to a protein that is not substantially similar to the Wnt-7B-like protein, e.g., a protein that is different from the Wnt-7B-like protein and that is derived from the same or a different organism. Within a Wnt-7B-like fusion protein the Wnt-7B-like polypeptide can correspond to all or a portion of a Wnt-7B-like protein. In one embodiment, a Wnt-7B-like fusion protein comprises at least one biologically active portion of a Wnt-7B-like protein. In another embodiment, a Wnt-7B-like fusion protein comprises at least two biologically active portions of a Wnt-7B-like protein. In yet another embodiment, a Wnt-7B-like fusion protein comprises at least three biologically active portions of a Wnt-7B-like protein. Within the fusion protein, the term "operatively linked" is intended to indicate that the Wnt-7B-like polypeptide and the non-Wnt-7B-like polypeptide are fused in-frame to each other. The non-Wnt-7B-like polypeptide can be fused to the N-terminus or C-terminus of the Wnt-7B-like polypeptide.

For example, in one embodiment a Wnt-7B-like fusion protein comprises a Wnt-7B-like domain operably linked to the extracellular domain of a second protein known to be involved in an activity of interest. Such fusion proteins can be further utilized in screening assays for compounds which modulate Wnt-7B-like activity (such assays are described in detail below).

In one embodiment, the fusion protein is a GST-Wnt-7B-like fusion protein in which the Wnt-7B-like sequences are fused to the C-terminus of the GST (i.e., glutathione S-transferase) sequences. Such fusion proteins can facilitate the purification of recombinant Wnt-7B-like.

In another embodiment, the fusion protein is a Wnt-7B-like protein containing a heterologous signal sequence at its N-terminus. In certain host cells (e.g., mammalian host cells), expression and/or secretion of Wnt-7B-like can be increased through use of a heterologous signal sequence.

In yet another embodiment, the fusion protein is a Wnt-7B-like-immunoglobulin fusion protein in which the Wnt-7B-like sequences comprising primarily the extracellular domains are fused to sequences derived from a member of the immunoglobulin protein family. The Wnt-7B-like-immunoglobulin fusion proteins of the invention can be incorporated into pharmaceutical compositions and administered to a subject to inhibit an interaction between a Wnt-7B-like ligand and a Wnt-7B-like protein on the surface of a cell, to thereby suppress Wnt-7B-like-mediated signal transduction in vivo. The Wnt-7B-like-immunoglobulin fusion proteins can be used to affect the bioavailability of a Wnt-7B-like cognate ligand. Inhibition of the Wnt-7B-like ligand/Wnt-7B-like interaction may be useful therapeutically for both the treatment of proliferative and differentiative disorders, as well as modulating (e.g. promoting or inhibiting) cell survival. Moreover, the Wnt-7B-like-immunoglobulin fusion proteins of the invention can be used as immunogens to produce anti-Wnt-7B-like antibodies in a subject, to purify Wnt-7B-like ligands, and in screening assays to identify molecules that inhibit the interaction of Wnt-7B-like with a Wnt-7B-like ligand.

A Wnt-7B-like chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *CURRENT PROTOCOLS IN MOLECULAR BIOLOGY*, John Wiley & Sons, 1992). Moreover, many expression vectors are commercially available that already encode a fusion moiety (e.g., a GST polypeptide). A Wnt-7B-like-encoding nucleic acid can be cloned into such an expression vector such that the fusion moiety is linked in-frame to the Wnt-7B-like protein.

The invention also provides signal sequences derived from various Wnt-7B-like polypeptides. The signal sequences include, e.g., polypeptides including the signal peptides identified for the Wnt-7B-like polypeptides as predicted by the SignalP software program for the Wnt-7B-like polypeptides described above. These signal sequences are useful for directing a linked polypeptide sequence to a desired intracellular or extracellular (if secretion from the cell is desired) location. In some embodiments, the signal sequence includes a portion of a Wnt-7B-like signal sequence that is sufficient to direct a linked polypeptide to a desired cellular compartment.

Wnt-7B-like Agonists and Antagonists

The present invention also pertains to variants of the Wnt-7B-like proteins that function as either Wnt-7B-like agonists (mimetics) or as Wnt-7B-like antagonists. Variants of the Wnt-7B-like protein can be generated by mutagenesis, e.g., discrete point mutation or truncation of the Wnt-7B-like protein. An agonist of the Wnt-7B-like protein can retain substantially the same, or a subset of, the biological activities of the naturally occurring form of the Wnt-7B-like protein. An antagonist of the Wnt-7B-like protein can inhibit one or more of the activities of the naturally occurring form of the Wnt-7B-like protein by, for example, competitively binding to a downstream or upstream member of a cellular signaling cascade which includes the Wnt-7B-like protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Wnt-7B-like proteins.

Variants of the Wnt-7B-like protein that function as either Wnt-7B-like agonists (mimetics) or as Wnt-7B-like antagonists can be identified by screening combinatorial libraries of mutants, e.g., truncation mutants, of the Wnt-7B-like protein for Wnt-7B-like protein agonist or antagonist activity. In one embodiment, a variegated library of Wnt-7B-like variants is generated by combinatorial mutagenesis at the nucleic acid level and is encoded by a variegated gene library. A variegated library of Wnt-7B-like variants can be produced by, for example, enzymatically ligating a mixture of synthetic oligonucleotides into gene sequences such that a degenerate set of potential Wnt-7B-like sequences is expressible as individual polypeptides, or alternatively, as a set of larger fusion proteins (e.g., for phage display) containing the set of Wnt-7B-like sequences therein. There are a variety of methods which can be used to produce libraries of potential Wnt-7B-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Wnt-7B-like sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1 983) *Nuc Acid Res* 11:477.

Polypeptide Libraries

In addition, libraries of fragments of the Wnt-7B-like protein coding sequence can be used to generate a variegated population of Wnt-7B-like fragments for screening and subsequent selection of variants of a Wnt-7B-like protein. In one embodiment, a library of coding sequence fragments can be generated by treating a double stranded PCR fragment of a Wnt-7B-like coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the Wnt-7B-like protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Wnt-7B-like proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify Wnt-7B-like variants (Arkin and Yourvan (1992) *PNAS* 89:7811–7815; Delgrave et al. (1993) *Protein Engineering* 6:327–331).

In one embodiment, cell based assays can be exploited to analyze a variegated Wnt-7B-like library, e.g., a library of mutant Wnt-7B-like polypeptides. For example, a library of expression vectors can be transfected into a cell line that ordinarily responds to a particular ligand or receptor in a Wnt-7B-like-dependent manner, e.g., through a signaling complex. The transfected cells are then contacted with the putative Wnt-7B-like interactant and the effect of expression of the mutant Wnt-7B-like on signaling by the signaling complex can be detected, e.g. by measuring a cellular activity or cell survival. Plasmid DNA can then be recovered from the cells which score for inhibition, or alternatively, potentiation of, e.g., cytokine induction, and the individual clones further characterized.

Anti-Wnt-7B-like Antibodies

The invention also includes antibodies to a Wnt-7B-like polypeptide. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$, and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of Wnt-7B-like that is located on the surface of the protein, e.g., a hydrophilic region. A hydrophobicity analysis of the human Wnt-7B-like protein sequence will indicate which regions of a Wnt-7B-like polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad Sci. USA* 78: 3824–3828; Kyte and Doolittle 1982, *J Mol. Biol.* 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund’s (complete and incomplete), mineral gels (e.g., aluminum hydroxide), surface active substances (e.g., lysolecithin, pluronic.polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding,1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: *MONOCLONAL ANTIBODIES AND CANCER THERAPY*, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: *MONOCLONAL ANTIBODIES AND CANCER THERAPY*, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al,(*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication W094/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

Techniques can also be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an Fab fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Also provided are bispecific antibodies. Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc R), such as Fc RI (CD64), Fc RII (CD32) and Fc RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity can also be prepared using heterobifunctional cross-linkers as described in Wolff et al. *Cancer Research*, 53: 2560–2565 (1993). Alternatively, an antibody can be engineered that has dual Fc regions and can thereby have enhanced complement lysis and ADCC capabilities. See Stevenson et al., *Anti-Cancer Drug Design.* 3: 219–230 (1989).

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Nati Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes iiclude horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington : The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90:

7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg1kg body weight. Common dosing frequencies may range, for example, from twice daily to once a week.

Wnt-7B-like Recombinant Expression Vectors and Host Cells

Another aspect of the invention pertains to vectors, preferably expression vectors, containing a nucleic acid encoding a Wnt-7B-like protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *GENE EXPRESSION TECHNOLOGY: METHODS IN ENZYMOLOGY* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Wnt-7B-like proteins, mutant forms of Wnt-7B-like, fusion proteins, etc.).

The recombinant expression vectors of the invention can be designed for expression of Wnt-7B-like in prokaryotic or eukaryotic cells. For example, Wnt-7B-like can be expressed in bacterial cells such as *E. coli*, insect cells (using baculovirus expression vectors) yeast cells or mammalian cells. Suitable host cells are discussed further in Goeddel, *GENE EXPRESSION TECHNOLOGY: METHODS IN ENZYMOLOGY* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., *GENE EXPRESSION TECHNOLOGY: METHODS IN ENZYMOLOGY* 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, *GENE EXPRESSION TECHNOLOGY: METHODS IN ENZYMOLOGY* 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the Wnt-7B-like expression vector is a yeast expression vector. Examples of vectors for expression in yeast *S. cerivisae* include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp., San Diego, Calif.).

Alternatively, Wnt-7B-like can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165). and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., *MOLECULAR CLONING: A LABORATORY MANUAL*. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1 983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to Wnt-7B-like mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Wnt-7B-like protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*MOLECULAR CLONING: A LABORATORY MANUAL*. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding Wnt-7B-like or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Wnt-7B-like protein. Accordingly, the invention further provides methods for producing Wnt-7B-like protein using the host cells of the invention. In one embodiment, the method comprises culturing the host cell of invention (into which a recombinant expression vector encoding Wnt-7B-like has been introduced) in a suitable medium such that Wnt-7B-like protein is produced. In another embodiment, the method further comprises isolating Wnt-7B-like from the medium or the host cell.

Transgenic Animals

Host cells of the invention can also be used to produce nonhuman transgenic animals. For example, in one embodiment, a host cell of the invention is a fertilized oocyte or an embryonic stem cell into which Wnt-7B-like-coding sequences have been introduced. Such host cells can then be used to create non-human transgenic animals in which exogenous Wnt-7B-like sequences have been introduced into their genome or homologous recombinant animals in which endogenous Wnt-7B-like sequences have been altered. Such animals are useful for studying the function and/or activity of Wnt-7B-like and for identifying and/or evaluating modulators of Wnt-7B-like activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Wnt-7B-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Wnt-7B-like-encoding nucleic acid into the male pronuclei of a fertilized oocyte, e.g., by microinjection, retroviral infection, and allowing the oocyte to develop in a pseudopregnant female foster animal. The human Wnt-7B-like cDNA can be introduced as a transgene into the genome of a non-human animal. Alternatively, a nonhuman homologue of the human Wnt-7B-like gene, such as a mouse Wnt-7B-like gene, can be isolated based on hybridization to the human Wnt-7B-like cDNA (described further above) and used as a transgene. Intronic sequences and polyadenylation signals can also be included in the transgene to increase the efficiency of expression of the transgene. A tissue-specific regulatory sequence(s) can be operably linked to the Wnt-7B-like transgene to direct expression of Wnt-7B-like protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: *MANIPULATING THE MOUSE EMBRYO*, Cold Spring Harbor Laboratory Press, Cold Spring Harbor, N.Y. Similar methods are used for production of other transgenic animals. A transgenic founder animal can be identified based upon the presence of the Wnt-7B-like transgene in its genome and/or expression of Wnt-7B-like mRNA in tissues or cells of the animals. A transgenic founder animal can then be used to breed additional animals carrying the transgene. Moreover, transgenic animals carrying a transgene encoding Wnt-7B-like can further be bred to other transgenic animals carrying other transgenes.

To create a homologous recombinant animal, a vector is prepared which contains at least a portion of a Wnt-7B-like gene into which a deletion, addition or substitution has been introduced to thereby alter, e.g., functionally disrupt, the Wnt-7B-like gene. The Wnt-7B-like gene can be a human gene (e.g., the cDNA of SEQ ID NO:1), but more preferably, is a non-human homologue of a human Wnt-7B-like gene. For example, a mouse homologue of human Wnt-7B-like gene of, e.g., SEQ ID NO:29, can be used to construct a homologous recombination vector suitable for altering an endogenous Wnt-7B-like gene in the mouse genome. In one embodiment, the vector is designed such that, upon homologous recombination, the endogenous Wnt-7B-like gene is functionally disrupted (i.e., no longer encodes a functional protein; also referred to as a "knock out" vector).

Alternatively, the vector can be designed such that, upon homologous recombination, the endogenous Wnt-7B-like gene is mutated or otherwise altered but still encodes functional protein (e.g., the upstream regulatory region can be altered to thereby alter the expression of the endogenous Wnt-7B-like protein). In the homologous -recombination vector, the altered portion of the Wnt-7B-like gene is flanked at its 5' and 3' ends by additional nucleic acid of the Wnt-7B-like gene to allow for homologous recombination to occur between the exogenous Wnt-7B-like gene carried by the vector and an endogenous Wnt-7B-like gene in an embryonic stem cell. The additional flanking Wnt-7B-like nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced Wnt-7B-like gene has homologously recombined with the endogenous Wnt-7B-like gene are selected (see e.g., Li et al. (1992) *Cell* 69:915).

The selected cells are then injected into a blastocyst of an animal (e.g., a mouse) to form aggregation chimeras. See e.g., Bradley 1987, In: *TERATOCARCINOMAS AND EMBRYONIC STEM CELLS: A PRACTICAL APPROACH*, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The Wnt-7B-like nucleic acid molecules, Wnt-7B-like proteins, and anti-Wnt-7B-like antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Wnt-7B-like protein or anti-Wnt-7B-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Uses and Methods of the Invention

The nucleic acid molecules, proteins, protein homologues, and antibodies described herein that include extracellular and transmembrane domains and, therefore, can be used in one or more of the following methods: (a) screening assays; (b) detection assays (e.g., chromosomal mapping, tissue typing, forensic biology), (c) predictive medicine (e.g., diagnostic assays, prognostic assays, monitoring clinical trials, and pharmacogenomics); and (d) methods of treatment (e.g., therapeutic and prophylactic). A Wnt-7B-like protein interacting with other cellular proteins can thus be used to (i) modulate that respective protein activity; (ii) regulate cellular proliferation; (iii) regulate cellular differentiation; and (iv) regulate cell survival.

The isolated nucleic acid molecules of the invention can be used to express Wnt-7B-like protein (e.g., via a recombinant expression vector in a host cell in gene therapy applications), to detect Wnt-7B-like mRNA (e.g., in a biological sample) or a genetic lesion in a Wnt-7B-like gene, and to modulate Wnt-7B-like activity, as described further below. In addition, the Wnt-7B-like proteins can be used to screen drugs or compounds that modulate the Wnt-7B-like activity or expression as well as to treat disorders characterized by insufficient or excessive production of Wnt-7B-like protein or production of Wnt-7B-like protein forms that have decreased or aberrant activity compared to Wnt-7B-like wild type protein (e.g. proliferative disorders such as cancer or preclampsia, or any disease or disorder described in Sections 1–14 above). In addition, the anti-Wnt-7B-like antibodies of the invention can be used to detect and isolate Wnt-7B-like proteins and modulate Wnt-7B-like activity.

This invention further pertains to novel agents identified by the above described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) that bind to Wnt-7B-like proteins or have a stimulatory or inhibitory effect on, for example, Wnt-7B-like expression or Wnt-7B-like activity.

In one embodiment, the invention provides assays for screening candidate or test compounds which bind to or modulate the activity of the membrane-bound form of a Wnt-7B-like protein or polypeptide or biologically active portion thereof. The test compounds of the present invention can be obtained using any of the numerous approaches in combinatorial library methods Known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *BioTechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of Wnt-7B-like protein, or a biologically active portion thereof, on the cell surface is contacted with a test compound and the ability of the test compound to bind to a Wnt-7B-like protein determined. The cell, for example, can of mammalian origin or a yeast cell. Determining the ability of the test compound to bind to the Wnt-7B-like protein can be accomplished, for example, by coupling the test compound with a radioisotope or enzymatic label such that binding of the test compound to the Wnt-7B-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of Wnt-7B-like protein, or a biologically active portion thereof, on the cell surface with a known compound which binds Wnt-7B-like to form an assay mixture, contacting the assay mixture with a test compound, and determining the ability of the test compound to interact with a Wnt-7B-like protein, wherein determining the ability of the test compound to interact with a Wnt-7B-like protein comprises determining the ability of the test compound to preferentially bind to Wnt-7B-like or a biologically active portion thereof as compared to the known compound.

In another embodiment, an assay is a cell-based assay comprising contacting a cell expressing a membrane-bound form of Wnt-7B-like protein, or a biologically active portion thereof, on the cell surface with a test compound and determining the ability of the test compound to modulate (e.g., stimulate or inhibit) the activity of the Wnt-7B-like protein or biologically active portion thereof. Determining the ability of the test compound to modulate the activity of Wnt-7B-like or a biologically active portion thereof can be accomplished, for example, by determining the ability of the Wnt-7B-like protein to bind to or interact with a Wnt-7B-like target molecule. As used herein, a "target molecule" is a molecule with which a Wnt-7B-like protein binds or interacts in nature, for example, a molecule on the surface of a cell which expresses a Wnt-7B-like interacting protein, a molecule on the surface of a second cell, a molecule in the extracellular milieu, a molecule associated with the internal surface of a cell membrane or a cytoplasmic molecule. A Wnt-7B-like target molecule can be a non-Wnt-7B-like molecule or a Wnt-7B-like protein or polypeptide of the present invention. In one embodiment, a Wnt-7B-like target molecule is a component of a signal transduction pathway that facilitates transduction of an extracellular signal (e.g. a signal generated by binding of a compound to a membrane-bound Wnt-7B-like molecule) through the cell membrane and into the cell. The target, for example, can be a second intercellular protein that has catalytic activity or a protein that facilitates the association of downstream signaling molecules with Wnt-7B-like.

Determining the ability of the Wnt-7B-like protein to bind to or interact with a Wnt-7B-like target molecule can be accomplished by one of the methods described above for determining direct binding. In one embodiment, determining the ability of the Wnt-7B-like protein to bind to or interact with a Wnt-7B-like target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a Wnt-7B-like-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a Wnt-7B-like protein or biologically active portion thereof with a test compound and determining the ability of the test compound to bind to the Wnt-7B-like protein or biologically active portion thereof. Binding of the test compound to the Wnt-7B-like protein can be determined either directly or indirectly as described above. In one embodiment, the assay comprises contacting the Wnt-7B-like protein or biologically active portion thereof with a known compound which binds Wnt-7B-like to form an assay mixture, contacting the assay mixture with a test compound, and determining the ability of the test compound to interact with a Wnt-7B-like protein, wherein determining the ability of the test compound to interact with a Wnt-7B-like protein comprises determining the ability of the test compound to preferentially bind to Wnt-7B-like or biologically active portion thereof as compared to the known compound.

In another embodiment, an assay is a cell-free assay comprising contacting Wnt-7B-like protein or biologically active portion thereof with a test compound and determining the ability of the test compound to modulate (e.g. stimulate or inhibit) the activity of the Wnt-7B-like protein or biologically active portion thereof. Determining the ability of the test compound to modulate the activity of Wnt-7B-like can be accomplished, for example, by determining the ability of the Wnt-7B-like protein to bind to a Wnt-7B-like target molecule by one of the methods described above for determining direct binding. In an alternative embodiment, determining the ability of the test compound to modulate the activity of Wnt-7B-like can be accomplished by determining the ability of the Wnt-7B-like protein further modulate a Wnt-7B-like target molecule. For example, the catalytic/enzymatic activity of the target molecule on an appropriate substrate can be determined as previously described.

In yet another embodiment, the cell-free assay comprises contacting the Wnt-7B-like protein or biologically active portion thereof with a known compound which binds Wnt-7B-like to form an assay mixture, contacting the assay mixture with a test compound, and determining the ability of the test compound to interact with a Wnt-7B-like protein, wherein determining the ability of the test compound to interact with a Wnt-7B-like protein comprises determining the ability of the Wnt-7B-like protein to preferentially bind to or modulate the activity of a Wnt-7B-like target molecule.

The cell-free assays of the present invention are amenable to use of both the soluble form or the membrane-bound form of Wnt-7B-like. In the case of cell-free assays comprising the membrane-bound form of Wnt-7B-like, it may be desirable to utilize a solubilizing agent such that the membrane-bound form of Wnt-7B-like is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl--N,N-dimethyl-3-ammonio-1-propane sulfonate, 3-(3-cholamidopropyl)dimethylamminiol- 1-propane sulfonate (CHAPS), or 3-(3-cholamidopropyl)dimethylamminiol-2-hydroxy-1-propane sulfonate (CHAPSO).

In more than one embodiment of the above assay methods of the present invention, it may be desirable to immobilize either Wnt-7B-like or its target molecule to facilitate separation of complexed from uncomplexed forms of one or both of the proteins, as well as to accommodate automation of the assay. Binding of a test compound to Wnt-7B-like, or interaction of Wnt-7B-like with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-Wnt-7B-like fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or Wnt-7B-like protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Wnt-7B-like binding or activity determined using standard techniques.

Other techniques for immobilizing proteins on matrices can also be used in the screening assays of the invention. For example, either Wnt-7B-like or its target molecule can be immobilized utilizing conjugation of biotin and streptavidin. Biotinylated Wnt-7B-like or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Wnt-7B-like or target molecules, but which do not interfere with binding of the Wnt-7B-like protein to its target molecule, can be derivatized to the wells of the plate, and unbound target or Wnt-7B-like trapped in the wells by antibody conjugation. Methods for detecting such complexes, in addition to those described above for the GST-immobilized complexes, include immunodetection of complexes using antibodies reactive with the Wnt-7B-like or target molecule, as well as enzyme-linked assays that rely on detecting an enzymatic activity associated with the Wnt-7B-like or target molecule.

In another embodiment, modulators of Wnt-7B-like expression are identified in a method wherein a cell is contacted with a candidate compound and the expression of Wnt-7B-like mRNA or protein in the cell is determined. The level of expression of Wnt-7B-like mRNA or protein in the presence of the candidate compound is compared to the level of expression of Wnt-7B-like mRNA or protein in the absence of the candidate compound. The candidate compound can then be identified as a modulator of Wnt-7B-like expression based on this comparison. For example, when expression of Wnt-7B-like mRNA or protein is greater (statistically significantly greater) in the presence of the candidate compound than in its absence, the candidate compound is identified as a stimulator of Wnt-7B-like mRNA or protein expression. Alternatively, when expression of Wnt-7B-like mRNA or protein is less (statistically significantly less) in the presence of the candidate compound than in its absence, the candidate compound is identified as an inhibitor of Wnt-7B-like mRNA or protein expression. The level of Wnt-7B-like mRNA or protein expression in the cells can be determined by methods described herein for detecting Wnt-7B-like mRNA or protein.

In yet another aspect of the invention, the Wnt-7B-like proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) BioTechniques 14:920–924; Iwabuchi et al. (1993) Oncogene 8:1693–1696; and Brent WO94/10300), to identify other proteins that bind to or interact with Wnt-7B-like ("Wnt-7B-like-binding proteins" or "Wnt-7B-like-bp") and modulate Wnt-7B-like activity. Such Wnt-7B-like-binding proteins are also likelyto be involved in the propagation of signals by the Wnt-7B-like proteins as, for example, upstream or downstream elements of the Wnt-7B-like pathway.

The two-hybrid system is based on the modular nature of most transcription factors, which consist of separable DNA-binding and activation domains. Briefly, the assay utilizes two different DNA constructs. In one construct, the gene that codes for Wnt-7B-like is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Wnt-7B-like-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with Wnt-7B-like.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the Wnt-7B-like, sequences, described herein, can be used to map the location of the Wnt-7B-like genes, respectively, on a chromosome. The mapping of the Wnt-7B-like sequences to chromosomes is an important first step in correlating these sequences with genes associated with disease.

Briefly, Wnt-7B-like genes can be mapped to chromosomes by preparing PCR primers (preferably 15–25 bp in length) from the Wnt-7B-like sequences. Computer analysis of the Wnt-7B-like, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the Wnt-7B-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybridsis a rapid procedure for assigning a particular sequence to a particular chromosome. Three or more sequences can be assigned per day using a single thermal cycler. Using the Wnt-7B-like sequences to design oligonucleotide primers, sublocalization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see Verma et al., *HUMAN CHROMOSOMES: A MANUAL OF BASIC TECHNIQUES* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, for example, in McKusick, *MENDELIAN INHERITANCE IN MAN*, available on-line through Johns Hopkins University Welch Medical Library). The relationship between genes and disease, mapped to the same chromosomal region, can then be identified through linkage analysis (co-inheritance of physically adjacent genes), described in, for example, Egeland et al. (1987) *Nature*, 325:783–787.

Moreover, differences in the DNA sequences between individuals affected and unaffected with a disease associated with the Wnt-7B-like gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The Wnt-7B-like sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the Wnt-7B-like sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Wnt-7B-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers that each yield a noncoding amplified sequence of 100 bases. If predicted coding sequences are used, a more appropriate number of primers for positive individual identification would be 500–2,000.

A further use of the Wnt-7B-like sequences is to identify a cell or tissue type in a biological sample. As discussed above, various Wnt-7B-like genes are expressed in one or more cell types. Thus, a cell type can be identified based on the presence of RNA molecules from one or more Wnt-7B-like genes. Tissue distribution of various Wnt-7B-like genes are shown and discussed in FIGS. 19–23 and Examples 6–11, below.

Use of Wnt-7B-like Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, that can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of Wnt-7B-like gene are particularly appropriate for this use, as greater numbers of polymorphisms occur in the noncoding regions, making it easier to differentiate individuals using this technique. Examples of polynucleotide reagents include the Wnt-7B-like sequences or portions thereof, e.g., fragments derived from the noncoding regions of a Wnt-7B-like gene described herein, having a length of at least 20 bases, preferably at least 30 bases.

The Wnt-7B-like sequences described herein can further be used to provide polynucleotide reagents, e.g., labeled or labelable probes that can be used, for example, in an in situ hybridization technique, to identify a specifictissue, e.g., brain tissue, etc. This can be very useful in cases where a forensic pathologist is presented with a tissue of unknown origin. Panels of such Wnt-7B-like probes can be used to identify tissue by species and/or by organ type.

In a similar fashion, these reagents, e.g., Wnt-7B-like primers or probes can be used to screen tissue culture for contamination (i.e. screen for the presence of a mixture of different types of cells in a culture).

Determination of the Biological Effect of the Therapeutic

In various embodiments of the present invention, suitable in vitro or in vivo assays are utilized to determine the effect of a specific Therapeutic and whether its administration is indicated for treatment of the affected tissue.

In various specific embodiments, in vitro assays may be performed with representative cells of the type(s) involved in the:patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Malignancies

Wnt-7B-like proteins are located at the cellular membrane and are thought to be involved in the regulation of cell proliferation and differentiation. Accordingly, Therapeutics of the present invention may be useful in the therapeutic or prophylactic treatment of diseases or disorders that are associated with cell hyperproliferation and/or loss of control of cell proliferation (e.g., cancers, malignancies and tumors). For a review of such hyperproliferation disorders, see e.g., Fishman, et al., 1985. MEDICINE, 2nd ed., J.B. Lippincott Co., Philadelphia, Pa.

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) activity, that cancer or malignancy may subsequently be treated or prevented by the administration of a Therapeutic that serves to modulate protein ftmction.

Premalignant Conditions

The Therapeutics of the present invention that are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. BASIC PATHOLOGY, 2nd ed., W.B. Saunders Co., Philadelphia, Pa.

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic that possesses the ability to modulate activity of An aforementioned protein. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 kDal cell-surface protein, and the like. See e.g., Richards, et al, 1986. MOLECULAR PATHOLOGY, W.B. Saunders Co., Philadelphia, Pa.

In a specific embodiment of the present invention, a patient that exhibits one or more of the following predisposing factors for malignancy is treated by administration of an effective amount of a Therapeutic: (i) a chromosomal translocation associated with a malignancy (e.g., the Philadelphia chromosome (bcr/abl) for chronic myelogenous leukemia and t(14;18) for follicular lymphoma, etc.); (ii) familial polyposis or Gardner's syndrome (possible forerunners of colon cancer); (iii) monoclonal gammopathy of undetermined significance (a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, Peutz-Jeghers syndrome, neurofibromatosis of Von Recklinghausen, medullary thyroid carcinoma with amyloid production and pheochromocytoma, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another embodiment, a Therapeutic of the present invention is administered to a human patient to prevent the progression to breast, colon, lung, pancreatic, or uterine cancer, or melanoma or sarcoma.

Hyperproliferative and Dysproliferative Disorders

In one embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g, benign prostatic hypertrophy).

Neurodegenerative Disorders

Wnt-7B-like protein have been implicated in the deregulation of cellular maturation and apoptosis, which are both characteristic of neurodegenerative disease. Accordingly, Therapeutics of the invention, particularly but not limited to those that modulate (or supply) activity of an aforementioned protein, may be effective in treating or preventing neurodegenerative disease. Therapeutics of the present invention that modulate the activity of an aforementioned protein involved in neurodegenerative disorders can be assayed by any method known in the art for efficacy in treating or preventing such neurodegenerative diseases and disorders. Such assays include in vitro assays for regulated cell maturation or inhibition of apoptosis or in vivo assays using animal models of neurodegenerative diseases or disorders, or any of the assays described below. Potentially effective Therapeutics, for example but not by way of limitation, promote regulated cell maturation and prevent cell apoptosis in culture, or reduce neurodegeneration in animal models in comparison to controls.

Once a neurodegenerative disease or disorder has been shown to be amenable to treatment by modulation activity, that neurodegenerative disease or disorder can be treated or prevented by administration of a Therapeutic that modulates activity. Such diseases include all degenerative disorders involved with aging, especially osteoarthritis and neurodegenerative disorders.

Disorders Related to Organ Transplantation

Wnt-7B-like has been implicated in disorders related to organ transplantation, in particular but not limited to organ rejection. Therapeutics of the invention, particularly those that modulate (or supply) activity, may be effective in treating or preventing diseases or disorders related to organ transplantation. Therapeutics of the invention (particularly Therapeutics that modulate the levels or activity of an aforementioned protein) can be assayed by any method known in the art for efficacy in treating or preventing such diseases and disorders related to organ transplantation. Such assays include in vitro assays for using cell culture models as described below, or in vivo assays using animal models of diseases and disorders related to organ transplantation, see e.g., below. Potentially effective Therapeutics, for example but not by way of limitation, reduce immune rejection responses in animal models in comparison to controls.

Accordingly, once diseases and disorders related to organ transplantation are shown to be amenable to treatment by modulation of activity, such diseases or disorders can be treated or prevented by administration of a Therapeutic that modulates activity.

Cardiovascular Disease

Wnt-7B-like has been implicated in cardiovascular disorders, including in atherosclerotic plaque formation. Diseases such as cardiovascular disease, including cerebral thrombosis or hemorrhage, ischemic heart or renal disease, peripheral vascular disease, or thrombosis of other major vessel, and otherdiseases, including diabetes mellitus, hypertension, hypothyroidism, cholesterol ester storage disease, systemic lupus erythematosus, homocysteinemia, and familial protein or lipid processing diseases, and the like, are either directly or indirectly associated with atherosclerosis. Accordingly, Therapeutics of the invention, particularly those that modulate (or supply) activity or formation may be effective in treating or preventing atherosclerosis-associated diseases or disorders. Therapeutics of the invention (particularly Therapeutics that modulate the levels or activity) can be assayed by any method known in the art, including those described below, for efficacy in treating or preventing such diseases and disorders.

A vast array of animal and cell culture models exist for processes involved in atherosclerosis. A limited and non-exclusive list of animal models includes knockout mice for premature atherosclerosis (Kurabayashi and Yazaki, 1996, Int. Angiol. 15: 187–194), transgenic mouse models of atherosclerosis (Kappel et al., 1994, FASEB J. 8: 583–592), antisense oligonucleotide treatment of animal models (Callow, 1995, Curr. Opin. Cardiol. 10: 569–576), transgenic rabbit models for atherosclerosis (Taylor, 1997, Ann. N.Y. Acad. Sci 811: 146–152), hypercholesterolemic animal models (Rosenfeld, 1996, Diabetes Res. Clin. Pract. 30 Suppl.: 1–11), hyperlipidemic mice (Paigen et al., 1994, Curr. Opin. Lipidol. 5: 258–264), and inhibition of lipoxygenase in animals (Sigal et al., 1994, Ann. N.Y. Acad. Sci. 714: 211–224). In addition, in vitro cell models include but are not limited to monocytes exposed to low density lipoprotein (Frostegard et aL, 1996, Atherosclerosis 121: 93–103), cloned vascular smooth muscle cells (Suttles et al., 1995, Exp. Cell Res. 218: 331–338), endothelial cell-derived chemoattractant exposed T cells (Katz et al., 1994, J. Leukoc. Biol. 55: 567–573), cultured human aortic endothelial cells (Farber et al., 1992, Am. J. Physiol. 262: H1088–1085), and foam cell cultures (Libby et al., 1996, Curr Opin Lipidol 7: 330–335). Potentially effective Therapeutics, for example but not by way of limitation, reduce foam cell formation in cell culture models, or reduce atherosclerotic plaque formation in hypercholesterolemic mouse models of atherosclerosis in comparison to controls.

Accordingly, once an atherosclerosis-associated disease or disorder has been shown to be amenable to treatment by modulation of activity or formation, that disease or disorder can be treated or prevented by administration of a Therapeutic that modulates activity.

Cytokine and Cell Proliferation/Differentiation Activity

A Wnt-7B-like protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods: Assays for T-cell or thymocyte proliferation include without limitation those described in: CURRENT PROTOCOLS IN IMMUNOLOGY, Ed by Coligan et al., Greene Publishing Associates and Wiley-Interscience (Chapter 3 and Chapter 7); Takai et al., *J Immunol* 137:3494–3500, 1986; Bertagnoili et al., *J Immunol* 145:1706–1712, 1990; Bertagnolli et al., *Cell Immunol* 133:327–341, 1991; Bertagnolli, et al., *J Immunol* 149:3778–3783, 1992; Bowman et aL, *J Immunol* 152:1756–1761, 1994.

Assays for cytokine production and/or proliferation of spleen cells, lymph node cells or thymocytes include, without limitation, those described by Kruisbeek and Shevach, In: *CURRENT PROTOCOLS IN IMMUNOLOGY*. Coligan et al., eds. Vol 1, pp. 3.12.1–14, John Wiley and Sons, Toronto 1994; and by Schreiber, In: *CURRENT PROTOCOLS IN IMMUNOLOGY*. Coligan eds. Vol 1 pp. 6.8.1–8, John Wiley and Sons, Toronto 1994.

Assays for proliferation and differentiation of hematopoietic and lymphopoietic cells include, without limitation, those described by Bottomly et al., In: *CURRENT PROTOCOLS IN IMMUNOLOGY.* Coligan et al., eds. Vol 1 pp. 6.3.1–6.3.12, John Wiley and Sons, Toronto 1991; deVries et al., *J Exp Med* 173:1205–1211, 1991; Moreau et al, *Nature* 336:690–692, 1988; Greenberger et al., *Proc Natl Acad Sci U.S.A.* 80:2931–2938, 1983; Nordan, In: *CURRENT PROTOCOLS IN IMMUNOLOGY.* Coligan el al., eds. Vol 1 pp. 6.6.1–5, John Wiley and Sons, Toronto 1991; Smith et al., *Proc Natl AcadSci U.S.A.* 83:1857–1861, 1986; Measurement of human Interleukin 11-Bennett, et al. In: *CURRENT PROTOCOLS IN IMMUNOLOGY.* Coligan et al., eds. Vol 1 pp. 6.15.1 John Wiley and Sons, Toronto 1991; Ciarletta, et al., In: *CURRENT PROTOCOLS IN IMMUNOLOGY.* Coligan et al., eds. Vol 1 pp. 6.13.1, John Wiley and Sons, Toronto 1991.

Assays for T-cell clone responses to antigens (which will identify, among others, proteins that affect APC-T cell interactions as well as direct T-cell effects by measuring proliferation and cytokine production) include, without limitation, those described In: *CURRENT PROTOCOLS IN IMMUNOLOGY.* Coligan et al., eds., Greene Publishing Associates and Wiley-Interscience (Chapter 3Chapter 6, Chapter 7); Weinberger et al., *Proc Natl Acad Sci USA* 77:6091–6095, 1980; Weinberger et al., *Eur J Immun* 11:405–411, 1981; Takai et al., *J lmmunol* 137:3494–3500, 1986; Takai et al., *J lmmunol* 140:508–512, 1988.

Immune Stimulating or Suppressing Activity

A Wnt-7B-like protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by vital, bacterial, fungal or other infection may be treatable using a protein of the present invention, including infections by HIV, hepatitis viruses, herpesviruses, mycobacteria, Leishmania species., malaria species and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon re-exposure to specific antigen in the absence of the tolerizing agent.

Down regulating or preventing one or more antigen functions (including without limitation B lymphocyte antigen functions (such as, for example, B7), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to energize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA41g fusion proteins in vivo as described in Lenschow et al., *Science* 257:789–792 (1992) and Turka et al., *Proc Natl Acad Sci USA,* 89:11102–11105 (1992). In addition, murine models of GVHD (see Paul ed., *FUNDAMENTAL IMMUNOLOGY,* Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and auto-antibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of auto-antibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosis in MRL/1pr/1pr mice or NZB hybrid mice, murine autoimmune collagen arthritis, diabetes mellitus in NOD mice and BB rats, and murine experimental myasthenia gravis (see Paul ed., FUNDAMENTAL IMMUNOLOGY, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic vital diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-vital immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $β_2$ microglobulin protein or an MHC class II a chain protein and an MHC class II β chain protein to thereby express MHC class I or MHC class II proteins on the cell surface. Expression of the appropriate class I or class II iv1HC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods: Suitable assays for thymocyte or splenocyte cytotoxicity include, without limitation, those described In: CURRENT PROTOCOLS IN IMMUNOLOGY. Coligan e1al., eds. Greene Publishing Associates and Wiley-Interscience (Chapter 3, Chapter 7); Herrmann et al, *Proc Natl AcadSci USA* 78:2488–2492, 1981; Herrmann et aL, *J lmmunol* 128:1968–1974, 1982; Handa et al., *J Immunol* 135:1564–1572, 1985; Takai et al., *J Immunol* 137:3494–3500, 1986; Takai et al.,*J Immunol* 140:508–512, 1988; Herrmann et aL, *Proc Natl Acad Sci USA* 78:2488–2492, 1981; Herrmann et aL, *J lmmunol* 128:1968–1974, 1982; Handa etal., *J Immunol* 135:1564–1572, 1985; Takai et aL, *J Immunol* 137:3494–3500, 1986; Bowman et al., *J Virology* 61:1992–1998; Takai et al.,*J Immunol* 140:508–512, 1988; Bertagnolli et al, *Cell Immunol* 133:327–341, 1991; Brown et al., *J Immunol* 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J Immunol* 144:3028–3033, 1990; and Mond and Brunswick In: *CURRENT PROTOCOLS IN IMMUNOLOGY*. Coligan et al., (eds.) Vol 1 pp. 3.8.1–3.8.16, John Wiley and Sons, Toronto 1994.

Mixed lymphocyte reaction (MLR) assays (which will identify, among others, proteins that generate predominantly Th1 and CTL responses) include, without limitation, those described In: *CURRENT PROTOCOLS IN IMMUNOLOGY*. Coligan et al., eds. Greene Publishing Associates and Wiley-Interscience (Chapter 3, Chapter 7); Takai et al, *J Immunol* 137:3494–3500, 1986; Takai etal.,*J lmmunol* 140:508–512, 1988; Bertagnolli etal., *J Immunol* 149:3778–3783, 1992.

Dendritic cell-dependent assays (which will identify, among others, proteins expressed by dendritic cells that activate naive T-cells) include, without limitation, those described in: Guery et al., *J lmmunol* 134:536–544, 1995; Inaba et al,*J Exp Med* 173:549–559, 1991; Macatonia et al., *J Immunol* 154:5071–5079, 1995; Porgador et al.,*J Exp Med* 182:255–260, 1995; Nair et al.,*J Virol* 67:4062–4069, 1993; Huang et al, *Science* 264:961–965, 1994; Macatonia et al., *J Exp Med* 169:1255–1264, 1989; Bhardwaj et al., *J Clin Investig* 94:797–807, 1994; and Inaba et al., *J Exp Med* 172:631.–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795–808, 1992; Gorczyca et al., *Leukemia* 7:659–670, 1993; Gorczyca et al, *Cancer Res* 53:1945–1951, 1993; Itoh et al., *Cell* 66:233–243, 1991; Zacharchuk, *J Immunol* 145:4037–4045, 1990; Zamai et al., *Cytometry* 14:891–897, 1993; Gorczyca et al., *Internat J Oncol* 1:639–648, 1992.

Assays for proteins that influence early steps of T-cell commitment and development include, without limitation, those described in: Antica et al., Blood 84:111- 117, 1994; Fine et al., *Cell Immunol* 155: 111–122, 1994; Galy et al., *Blood* 85:2770–2778, 1995; Toki et al., *Proc Nat AcadSci USA* 88:7548–7551, 1991.

Hematopoiesis Regulating Activity

A Wnt-7B-like protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. *Cellular Biology* 15:141–151, 1995; Keller et al., *Mol. Cell. Biol* 13:473–486, 1993; McClanahan et al., *Blood* 81:2903–2915, 1993.

Assays for stem cell survival and differentiation (which will identify, among others, proteins that regulate lymphohematopoiesis) include, without limitation, those described in: Methylcellulose colony forming assays, Freshney, In: *CULTURE OF HEMATOPOIETIC CELLS*. Freshney, et al. (eds.) Vol pp. 265–268, Wiley-Liss, Inc., New York, N.Y. 1994; Hirayama et al., *Proc Natl Acad Sci USA* 89:5907–5911, 1992; McNiece and Briddeli, In: *CULTURE OF HEMATOPOIETIC CELLS*. Freshney, et al. (eds.) Vol pp. 23–39, Wiley-Liss, Inc., New York, N.Y. 1994; Neben et al., *Exp Hematol* 22:353–359, 1994; Ploemacher, In: *CULTURE OF HEMATOPOIETIC CELLS*. Freshney, et al. eds. Vol pp. 1–21, Wiley-Liss, Inc., New York, N.Y. 1994; Spooncer et al., In: *CULTURE OF HEMATOPOIETIC CELLS*. Freshhey, et al., (eds.) Vol pp. 163–179, Wiley-Liss, Inc., New York, N.Y. 1994; Sutherland, In: *CULTURE OF HEMATOPOIETIC CELLS*. Freshney, et al., (eds.) Vol pp. 139–162, Wiley-Liss, Inc., New York, N.Y. 1994.

Tissue Growth Activity

A Wnt-7B-like protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendonitis, carpal tunnel syndrome and other tendon or ligament defects. The compositions may also include an appropriate matrix and/or sequestering agent as a career as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. W095/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *EPIDERMAL WOUND HEALING*, pp. 71–112 (Maibach and Rovee, eds.), Year Book Medical Publishers, Inc., Chicago, as modified by Eaglstein and Menz, *J Invest. Dermatol* 71:382–84 (1978).

Activin/linhibin Activity

A Wnt-7B-like protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-b group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., *Endocrinology* 91:562–572, 1972; Ling et al., *Nature* 321:779–782, 1986; Vale et al., *Nature* 321:776–779, 1986; Mason et al., *Nature* 318:659–663, 1985; Forage et aL, *Proc Natl Acad Sci USA* 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by following methods. Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: *CURRENT PROTOCOLS IN IMMUNOLOGY*, Coligan et al., eds. (Chapter 6.12, *MEASUREMENT OF ALPHA AND BETA CHEMOKINES* 6.12.1–6.12.28); Taub et al. *J Clin Invest* 95:1370–1376, 1995; Lind et al. *APMIS* 103:140–146, 1995; Muller et al., *Eur J Immunol* 25: 1744–1748; Gruberet al. *J Immunol* 152:5860–5867, 1994; Johnston etal., *J Immunol* 153:1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., *J Clin. Pharmacol.* 26:131–140, 1986; Burdick et al., *Thrombosis Res.* 45:413–419, 1987; Humphrey et al., *Fibrinolysis* 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell–cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: *CURRENT PROTOCOLS IN IMMUNOLOGY*, Ed by Coligan, et al., Greene Publishing Associates and Wiley-Interscience (Chapter 7.28, Measurement of Cellular Adhesion under static conditions 7.28.1–7.28.22), Takai et al., *Proc Natl Acad Sci USA* 84:6864–6868, 1987; Bierer et al., *J Exp. Med.* 168:1145–1156, 1988; Rosenstein et al, *J Exp. Med.* 169:149–160 1989; Stoltenborg et al., *J Immunol Methods* 175:59–68, 1994; Stitt et al, *Cell* 80:661–670, 1995.

Anti-Inflammatory Activity

Proteins of the present invention may also exhibit anti-inflammatory activity. The anti-inflammatory activity may be achieved by providing a stimulus to cells involved in the nflammatory response, by inhibiting or promoting cell–cell interactions such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions),-including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining Wnt-7B-like protein and/or nucleic acid expression as well as Wnt-7B-like activity, in the context of a biological sample (e.g., blood, serum, cells, tissue) to thereby determine whether an individual is afflicted with a disease or disorder, or is at risk of developing a disorder, associated with aberrant Wnt-7B-like expression or activity. The invention also provides for prognostic (or predictive) assays for determining whether an individual is at risk of developing a disorder associated with Wnt-7B-like protein, nucleic acid expression or activity. For example, mutations in a Wnt-7B-like gene can be assayed in a biological sample. Such assays can be used for prognostic or predictive purpose to thereby prophylactically treat an individual prior to the onset of a disorder characterized by or associated with Wnt-7B-like protein, nucleic acid expression or activity.

Another aspect of the invention provides methods for determining Wnt-7B-like protein, nucleic acid expression or Wnt-7B-like activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of Wnt-7B-like in clinical trials.

These and other agents are described in further detail in the following sections.

Diagnostic Assays

An exemplary method for detecting the presenceor absence of Wnt-7B-like in a biological sample involves obtaining a biological sample from a test subject and contacting the biological sample with a compound or an agent capable of detecting Wnt-7B-like protein or nucleic acid (e.g., mRNA, genomic DNA) that encodes Wnt-7B-like protein such that the presence of Wnt-7B-like is detected in the biological sample. An agent for detecting Wnt-7B-like mRNA or genomic DNA is a labeled nucleic acid probe capable of hybridizing to Wnt-7B-like mRNA or genomic DNA. The nucleic acid probe can be, for example, a full-length Wnt-7B-like nucleic acid, or a portion thereof, such as an oligonucleotide of at least 15, 30, 50, 100, 250 or 500 nucleotides in length and sufficient to specifically hybridize under stringent conditions to Wnt-7B-like mRNA or genomic DNA. Other suitable probes for use in the diagnostic assays of the invention are described herein.

An agent for detecting Wnt-7B-like protein is an antibody capable of binding to Wnt-7B-like protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Wnt-7B-like mRNA, protein, or genomic DNA in a biological sample in vitro as well as in vivo. For example, in vitro techniques for detection of Wnt-7B-like mRNA include Northern hybridizations and in situ hybridizations. In vitro techniques for detection of Wnt-7B-like protein include enzyme linked immunosorbent assays (ELISAs), Western blots, immunoprecipitations and immunofluorescence. In vitro techniques for detection of Wnt-7B-like genomic DNA include Southern hybridizations. Furthermore, in vivo techniques for detection of Wnt-7B-like protein include introducing into a subject a labeled anti-Wnt-7B-like antibody. For example, the antibody can be labeled with a radioactive marker whose presence and location in a subject can be detected by standard imaging techniques.

In one embodiment, the biological :sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting Wnt-7B-like protein, mRNA, or genomic DNA, such that the presence of Wnt-7B-like protein, mRNA or genomic DNA is detected in the biological sample, and comparing the presence of Wnt-7B-like protein, mRNA or genomic DNA in the control sample with the presence of Wnt-7B-like protein, mRNA or genomic DNA in the test sample.

The invention also encompasses kit§ for detecting the presence of Wnt-7B-like in a biological sample. For example, the kit can comprise: a labeled compound or agent capable of detecting Wnt-7B-like protein or mRNA in a biological sample; means for determining the amount of Wnt-7B-like in the sample; and means for comparing the amount of Wnt-7B-like in the sample with a standard. The compound or agent can be packaged in a suitable container. The kit can further comprise instructions for using the kit to detect Wnt-7B-like protein or nucleic acid.

Prognostic Assays

The diagnostic methods described herein can furthermore be utilized to identify subjects having or at risk of developing a disease or disorder associated with aberrant Wnt-7B-like expression or activity. For example, the assays described herein, such as the preceding diagnostic assays or the following assays, can be utilized to identify a subject having or at risk of developing a disorder associated with Wnt-7B-like protein, nucleic acid expression or activity such as cancer or fibrotic disorders, or a Wnt-7B-like-specific disease as described in the individual sections 1–14, above. Alternatively, the prognostic assays can be utilized to identify a subject having or at risk for developing a disease or disorder. Thus, the present invention provides a method for identifying a disease or disorder associated with aberrant Wnt-7B-like expression or activity in which a test sample is obtained from a subject and Wnt-7B-like protein or nucleic acid (e.g., mRNA, genomic DNA) is detected, wherein the presence of Wnt-7B-like protein or nucleic acid is diagnostic for a subject having or at risk of developing a disease or disorder associated with aberrant Wnt-7B-like expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Wnt-7B-like expression or activity. For example, such methods can be used to determine whether a subject can be effectively treated with an agent for a disorder, such as cancer or preclampsia or a Wnt-7B-like-specific disease as described in the individual sections 1–14, above. Thus, the present invention provides methods for determining whether a subject can be effectively treated with an agent for a disorder associated with aberrant Wnt-7B-like expression or activity in which a test sample is obtained and Wnt-7B-like protein or nucleic acid is detected (e.g., wherein the presence of Wnt-7B-like protein or nucleic acid is diagnostic for a subject that can be administered the agent to treat a disorder associated with aberrant Wnt-7B-like expression or activity.)

The methods of the invention can also be used to detect genetic lesions in a Wnt-7B-like gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a Wnt-7B-like-protein, or the mis-expression of the Wnt-7B-like gene. For example, such genetic lesions can be detected by ascertaining the existence of at least one of (1) a deletion of one or more nucleotides from a Wnt-7B-like gene; (2) an addition of one or more nucleotides to a Wnt-7B-like gene; (3) a substitution of one or more nucleotides of a Wnt-7B-like gene, (4) a chromosomal rearrangement of a Wnt-7B-like gene; (5) an alteration in the level of a messenger RNA transcript of a Wnt-7B-like gene, (6) aberrant modification of a Wnt-7B-like gene, such as of the methylation pattern of the genomic DNA, (7) the presence of a non-wild type splicing pattern of a messenger RNA transcript of a Wnt-7B-like gene, (8) a non-wild type level of a Wnt-7B-like-protein, (9) allelic loss of a Wnt-7B-like gene, and (10) inappropriate post-translational modification of a Wnt-7B-like-protein. As described herein, there are a large number of assay techniques known in the art which can be used for detecting lesions in a Wnt-7B-like gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the Wnt-7B-like-gene (see Abravaya et al. (1995) Nucl Acids Res 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to a Wnt-7B-like gene under conditions such that hybridization and amplification of the Wnt-7B-like gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, Proc Natl Acad Sci USA 87:1874–1878), transcriptional amplification system (Kwoh, et al., 1989, Proc Natl Acad Sci USA 86:1173–1177), Q-Beta Replicase (Lizardi et al, 1988, Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Wnt-7B-like gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in Wnt-7B-like can be identified by hybridizing a sample and control nucleic acids, e.g., DNA or RNA, to high density arrays containing hundreds or thousands of oligonucleotides probes (Cronin et al. (1996) Human Mutation 7: 244–255; Kozal et al. (1996) Nature Medicine 2: 753–759). For example, genetic mutations in Wnt-7B-like can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Wnt-7B-like gene and detect mutations by comparing the sequence of the sample Wnt-7B-like with the corresponding wild-type (control) sequence. Examples of sequencing reactions include those based on techniques developed by Maxim and Gilbert (1977) PNAS 74:560 or Sanger (1977) PNAS 74:5463. It is also contemplated that any of a variety of automated sequencing procedures can be utilized when performing the diagnostic assays (Naeve et al., (1995) BioTechniques 19:448), including sequencing by mass spectrometry (see, e.g., PCT International Publ. No. WO 94/16101; Cohen et al. (1996) Adv Chromatogr 36:127–162; and Griffin et al. (1993) Appl Biochem Biotechnol 38:147–159).

Other methods for detecting mutations in the Wnt-7B-like gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type Wnt-7B-like sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Wnt-7B-like cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Wnt-7B-like sequence, e.g., a wild-type Wnt-7B-like sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Wnt-7B-like genes. For example, single strand conformation polymorphism (SSCP) may be used to detect differences in electrophoretic mobility between mutant and wild type nucleic acids (Orita et al. (1989) *Proc Natl Acad Sci USA*: 86:2766, see also Cotton (1993) *Mutat Res* 285:125–144; Hayashi (1992) *Genet Anal Tech Appl* 9:73–79). Single-stranded DNA fragments of sample and control Wnt-7B-like nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chein* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324: 163); Saiki et al. (1989) *Proc Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc Natl Acad Sci USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Wnt-7B-like gene.

Furthermore, any cell type or tissue, preferably peripheral blood leukocytes, in which Wnt-7B-like is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on Wnt-7B-like activity (e.g., Wnt-7B-like gene expression), as identified by a screening assay described herein can be administered to individuals to treat (prophylactically or therapeutically) disorders (e.g., cancer or gestational disorders or a Wnt-7B-like-specific disease as described in the individual sections 1–14, above) associated with aberrant Wnt-7B-like activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of Wnt-7B-like protein, expression of Wnt-7B-like nucleic acid, or mutation content of Wnt-7B-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, *Clin Exp Pharmacol Physiol*, 1996, 23:983–985 and Linder, *Clin Chem*, 1997, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of Wnt-7B-like protein, expression of Wnt-7B-like nucleic acid, or mutation content of Wnt-7B-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a Wnt-7B-like modulator, such as a modulator identified by one of the exemplary screening assays described herein.

Monitoring of Effects During Clinical Trials

Monitoring the influence of agents (e.g., drugs, compounds) on the expression or activity of Wnt-7B-like (e.g., the ability to modulate aberrant cell proliferation and/or differentiation) can be applied not only in basic drug screening, but also in clinical trials. For example, the effectiveness of an agent determined by a screening assay as described herein to increase Wnt-7B-like gene expression, protein levels, or upregulate Wnt-7B-like activity, can be monitored in clinical trails of subjects exhibiting decreased Wnt-7B-like gene expression, protein levels, or downregulated Wnt-7B-like activity. Alternatively, the effectiveness of an agent determined by a screening assay to decrease Wnt-7B-like gene expression, protein levels, or downregulate Wnt-7B-like activity, can be monitored in clinical trails of subjects exhibiting increased Wnt-7B-like gene expression, protein levels, or upregulated Wnt-7B-like activity. In such clinical trials, the expression or activity of Wnt-7B-like and, preferably, other genes that have been implicated in, for example, a cellular proliferation disorder or a Wnt-7B-like-specific disease as described in the individual sections 1–14, above, can be used as a "read out" or markers of the immune responsiveness of a particular cell.

For example, and not by way of limitation, genes, including Wnt-7B-like, that are modulated in cells by treatment with an agent (e.g., compound, drug or small molecule) that modulates Wnt-7B-like activity (e.g., identified in a screening assay as described herein) can be identified. Thus, to study the effect of agents on cellular proliferation disorders, for example, in a clinical trial, cells can be isolated and RNA prepared and analyzed for the levels of expression of Wnt-7B-like and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Wnt-7B-like or other genes. In this way, the gene expression pattern can serve as a marker, indicative of the physiological response of the cells to the agent. Accordingly, this response state may be determined before, and at various points during, treatment of the individual with the agent.

In one embodiment, the present invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a Wnt-7B-like protein, mRNA, or genomic DNA in the preadministration sample; (iii) obtaining one or more post-administration samples from the subject; (iv) detecting the level of expression or activity of the Wnt-7B-like protein, mRNA, or genomic DNA in the post-administration samples; (v) comparing the level of expression or activity of the Wnt-7B-like protein, mRNA, or genomic DNA in the pre-administration sample with the Wnt-7B-like protein, mRNA, or genomic DNA in the post administration sample or samples; and (vi) altering the administration of the agent to the subject accordingly. For example, increased administration of the agent may be desirable to increase the expression or activity of Wnt-7B-like to higher levels than detected, i.e., to increase the effectiveness of the agent. Alternatively, decreased administration of the agent may be desirable to decrease expression or activity of Wnt-7B-like to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant Wnt-7B-like expression or activity.

Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989, *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic Methods

In one aspect, the invention provides a method for preventing, in a subject, a disease or condition associated with an aberrant Wnt-7B-like expression or activity, by administering to the subject an agent that modulates Wnt-7B-like expression or at least one Wnt-7B-like activity. Subjects at risk for a disease that is caused or contributed to by aberrant Wnt-7B-like expression or activity can be identified by, for example, any or a combination of diagnostic or prognostic assays as described herein. Administration of a prophylactic agent can occur prior to the manifestation of symptoms characteristic of the Wnt-7B-like aberrancy, such that a disease or disorder is prevented or, alternatively, delayed in its progression. Depending on the type of Wnt-7B-like aberrancy, for example, a Wnt-7B-like agonist or Wnt-7B-like antagonist agent can be used for treating the subject. The appropriate agent can be determined based on screening assays described herein. The prophylactic methods of the present invention are further discussed in the following subsections.

Therapeutic Methods

Another aspect of the invention pertains to methods of modulating Wnt-7B-like expression or activity for therapeutic purposes. The modulatory method of the invention involves contacting a cell with an agent that modulates one or more of the activities of Wnt-7B-like protein activity associated with the cell. An agent that modulates Wnt-7B-like protein activity can be an agent as described herein, such as a nucleic acid or a protein, a naturally-occurring cognate ligand of a Wnt-7B-like protein, a peptide, a Wnt-7B-like peptidomimetic, or other small molecule. In one embodiment, the agent stimulates one or more Wnt-7B-like protein activity. Examples of such stimulatory agents include active Wnt-7B-like protein and a nucleic acid molecule encoding Wnt-7B-like that has been introduced into the cell. In another embodiment, the agent inhibits one or more Wnt-7B-like protein activity. Examples of such inhibitory agents include antisense Wnt-7B-like nucleic acid molecules and anti-Wnt-7B-like antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a Wnt-7B-like protein or nucleic acid molecule. In one embodiment, the method involves administering an agent (e.g., an agent identified by a screening assay described herein), or combination of agents that modulates (e.g., upregulates or downregulates) Wnt-7B-like expression or activity. In another embodiment, the method involves administering a Wnt-7B-like protein or nucleic acid molecule as therapy to compensate for reduced or aberrant Wnt-7B-like expression or activity.

Stimulation of Wnt-7B-like activity is desirable in situations in which Wnt-7B-like is abnormally downregulated and/or in which increased Wnt-7B-like activity is likely to have a beneficial effect. One example of such a situation is where a subject has a disorder characterized by aberrant cell proliferation and/or differentiation (e.g., cancer). Another example of such a situation is where the subject has a gestational disease (e.g., preclampsia). Other diseases of the invention include the Wnt-7B-like-specific diseases as described in the individual sections 1–14, above.

This invention is further illustrated by the following non-limiting examples.

EXAMPLES

Example 1

Expression of Clone 29518614 Nucleic Acid in Tissues Determined by TaqMan™ Analysis The expression of clone 29518614 nucleic acid was evaluated by real time quantitative PCR in tissues indicated in Table 2, below. The numbering in column 1 of Table 2 corresponds to the lane order of the histograms in FIGS. 3A–C.

TABLE 2

Panel of cell types used in TaqMan ™ Analysis

| | | |
|---|---|---|
| 1 | Endothelial cells | |
| 2 | Endothelial cells (treated) | |
| 3 | Pancreas | |
| 4 | Pancreatic ca. | CAPAN 2 |

TABLE 2-continued

Panel of cell types used in TaqMan ™ Analysis

| | | |
|---|---|---|
| 5 | Adipose | |
| 6 | Adrenal gland | |
| 7 | Thyroid | |
| 8 | Salivary gland | |
| 9 | Pituitary gland | |
| 10 | Brain (fetal) | |
| 11 | Brain (whole) | |
| 12 | Brain (amygdala) | |
| 13 | Brain (cerebellum) | |
| 14 | Brain (hippocampus) | |
| 15 | Brain (hypothalamus) | |
| 16 | Brain (substantia nigra) | |
| 17 | Brain (thalamus) | |
| 18 | Spinal cord | |
| 19 | CNS ca. (glio/astro) | U87-MG |
| 20 | CNS ca. (glio/astro) | U-118-MG |
| 21 | CNS ca. (astro) | SW1783 |
| 22 | CNS ca.* (neuro; met) | SK-N-AS |
| 23 | CNS ca. (astro) | SF-539 |
| 24 | CNS ca. (astro) | SNB-75 |
| 25 | CNS ca. (glio) | SNB-19 |
| 26 | CNS ca. (glio) | U251 |
| 27 | CNS ca. (glio) | SF-295 |
| 28 | Heart | |
| 29 | Skeletal muscle | |
| 30 | Bone marrow | |
| 31 | Thymus | |
| 32 | Spleen | |
| 33 | Lymph node | |
| 34 | Colon (ascending) | |
| 35 | Stomach | |
| 36 | Small intestine | |
| 37 | Colon ca. | SW480 |
| 38 | Colon ca.* (SW480 met) | SW620 |
| 39 | Colon ca. | HT29 |
| 40 | Colon ca. | HCT-116 |
| 41 | Colon ca. | CaCo-2 |
| 42 | Colon ca. | HCT-15 |
| 43 | Colon ca. | HCC-2998 |
| 44 | Gastric ca.* (liver met) | NCI-N87 |
| 45 | Bladder | |
| 46 | Trachea | |
| 47 | Kidney | |
| 48 | Kidney (fetal) | |
| 49 | Renal ca. | 786-0 |
| 50 | Renal ca. | A498 |
| 51 | Renal ca. | RXF 393 |
| 52 | Renal ca. | ACHN |
| 53 | Renal ca. | UO-31 |
| 54 | Renal ca. | TK-10 |
| 55 | Liver | |
| 56 | Liver (fetal) | |
| 57 | Liver ca. (hepatoblast) | HepG2 |
| 58 | Lung | |
| 59 | Lung (fetal) | |
| 60 | Lung ca. (small cell) | LX-1 |
| 61 | Lung ca. (small cell) | NCI-H69 |
| 62 | Lung ca. (s. cell var.) | SHP-77 |
| 63 | Lung ca. (large cell) | NCI-H460 |
| 64 | Lung ca. (non-sm. cell) | A549 |
| 65 | Lung ca. (non-s. cell) | NCI-H23 |
| 66 | Lung ca (non-s. cell) | HOP-62 |
| 67 | Lung ca. (non-s. cl) | NCI-H522 |
| 68 | Lung ca. (squam.) | SW 900 |
| 69 | Lung ca. (squam.) | NCI-H596 |
| 70 | Mammary gland | |
| 71 | Breast ca.* (pl. effusion) | MCF-7 |
| 72 | Breast ca.* (pl. ef) | MDA-MB-231 |
| 73 | Breast ca.* (pl. effusion) | T47D |
| 74 | Breast ca. | BT-549 |
| 75 | Breast ca. | MDA-N |
| 76 | Ovary | |
| 77 | Ovarian ca. | OVCAR-3 |
| 78 | Ovarian ca. | OVCAR-4 |
| 79 | Ovarian ca. | OVCAR-5 |
| 80 | Ovarian ca. | OVCAR-8 |
| 81 | Ovarian ca. | IGROV-1 |
| 82 | Ovarian ca.* (ascites) | SK-OV-3 |
| 83 | Myometrium | |
| 84 | Uterus | |
| 85 | Placenta | |
| 86 | Prostate | |
| 87 | Prostate ca.* (bone met) | PC-3 |
| 88 | Testis | |
| 89 | Melanoma | Hs688(A).T |
| 90 | Melanoma* (met) | Ms688(B).T |
| 91 | Melanoma | UACC-62 |
| 92 | Melanoma | M14 |
| 93 | Melanoma | LOX IMVI |
| 94 | Melanoma* (met) | SK-MEL-5 |
| 95 | Melanoma | SK-MEL-28 |
| 96 | Melanoma | UACC-257 |

In the PCR assay used, a fluorogenic probe, consisting of an oligonucleotide with both a reporter and a quencher dye attached, is annealed specifically to the target sequence between the forward and reverse primers. When the probe is cleaved by the 5' nuclease activity of the DNA polymerase, the reporter dye is separated from the quencher dye and a sequence-specific signal is generated. With each cycle, additional reporter dye molecules are cleaved from their respective probes, and the increase in fluorescence intensity is monitored during the PCR.

Probes and primers were designed according to Perkin Elmer Biosystem's Primer Express software package (version I for Apple Computer's Macintosh Power PC) using the sequence of 2777610 as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized, double HPLC purified to remove uncoupled dye and evaluated by mass spectroscopy for efficient coupling of reporter and quencher dyes to the 5' and 3' ends of the probe, respectively.

PCR conditions: Sample RNA was provided from a broad range of normal and tumor tissues. The RNA from each tissue (poly A+ RNA, 2.8 pg) and from the cell lines (total RNA, 70 ng) was spotted in each well of a 96 well PCR plate. PCR cocktails including the forward primer, reverse primer and a 2777610-specific probe (see below; and another set of primers and a probe for another gene to serve as a reference) were set up using 1 X TaqMan™ PCR Master Mix for the PE Biosystems 7700, with 5 mM MgCl2, dNTPs (dA, dG, dC, dU at 1:1:1:2 ratios), 0.25 U/ml AmpliTaq Gold™ (PE Biosystems), and 0.4 U/$\mu$l RNase inhibitor, and 0.25 U/$\mu$l reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

TaqMan probes and primers used in the analysis were:

Ag 316 (F): 5' -CCGGCCTCATTGTTATGCA-3' (SEQ ID NO:4)

Ag 316 (R): 5' -TCTCCCGGCGCTTCG-3' (SEQ ID NO:5)

Ag 316 (P): TET-5' -CGCGCGTTCTTCTTGATCT- CCCG-3' -TAMRA (SEQ ID NO:6)

Figure 3B:
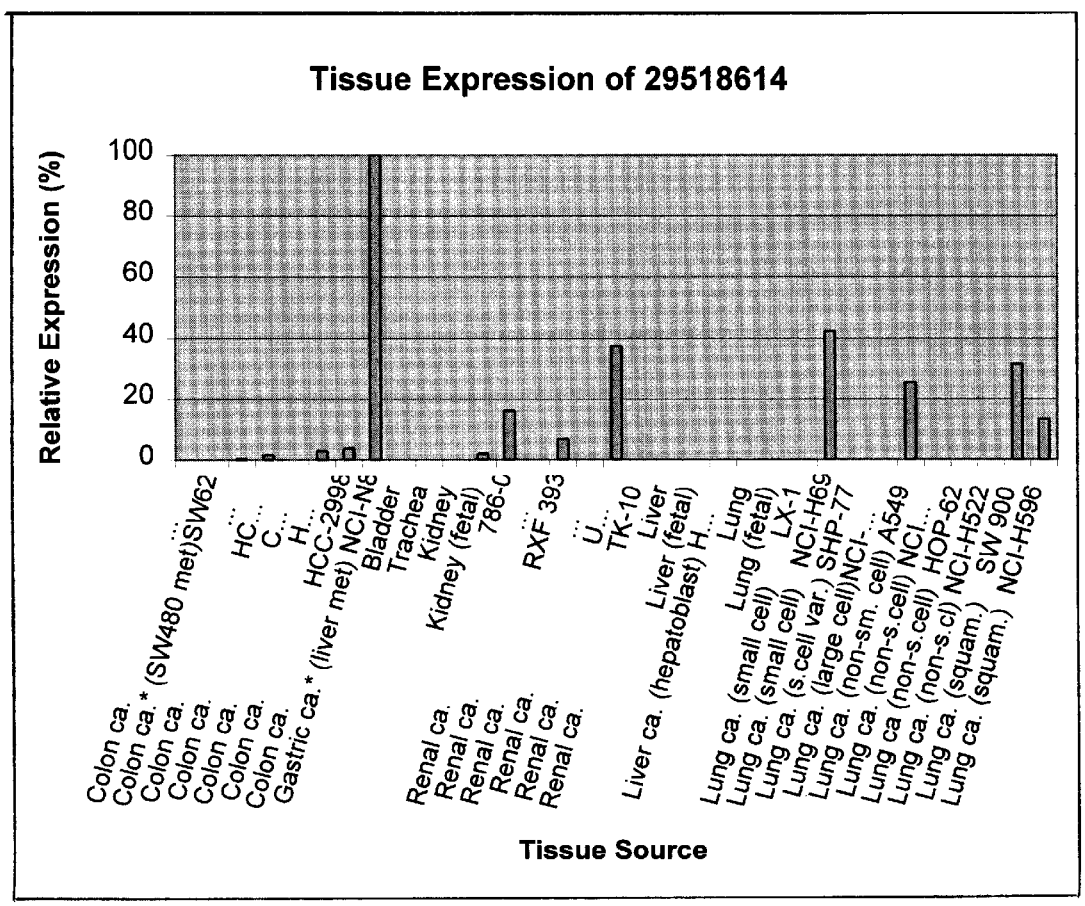
Figure 3C:
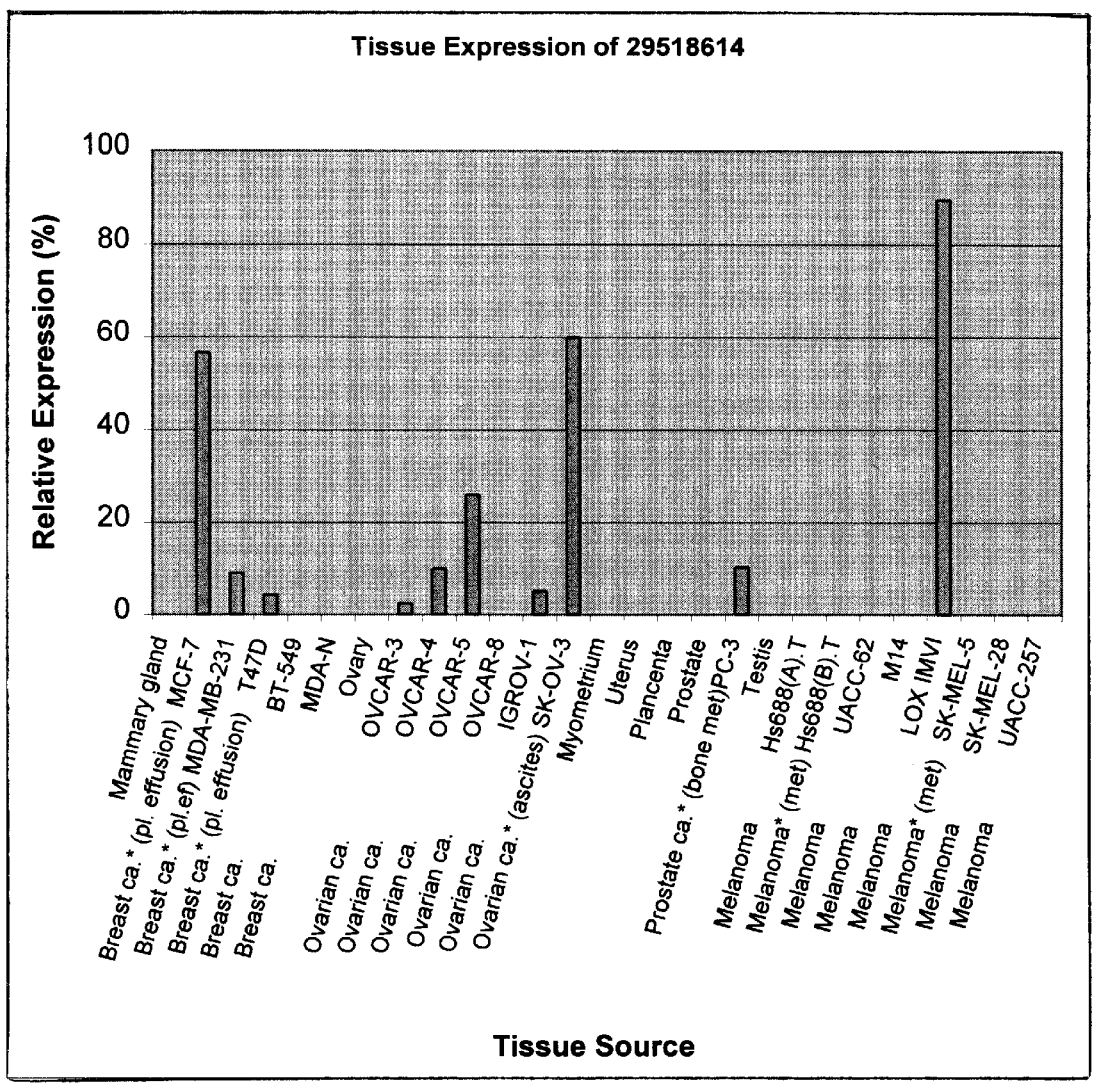

The TaqMan generated expression profile of 29518614 hWnt-7B shown in FIGS. 3A–C indicate there is high expression in multiple tumor cell lines from all major carcinoma groups.

Example 2

Production of Human Anti-Wnt-7B Antibody

Mice, designated as the transgenic Xenomouse™, are employed in this Example. The generation and characteristics of the Xenomouse™ are described in detail in PCT publication WO 94/02602.

A number of Xenomouse™ animals between 2 and 6 are immunized intraperitoneally with an immunogenic amount, approximately 20–60 microgram 29518614 polypeptide immunogen emulsified either in Freund's incomplete adjuvant or Freund's complete adjuvant. The mice receive at least 2 and up to 6 such immunizing injections at intervals of 2 to 3 weeks. Serum titers are determined after the second dose and following each dose thereafter. Blood is obtained from the retrobulbar plexus approximately 1 week after the injections to be monitored.

The titer of immune specific serum is determined using an enzyme linked immunosorbent assay. For this purpose, the 29518614 antigen is immobilized to the wells of assay microtiter plates by adding a solution containing 100–500 ng of the antigen and incubating either at 4° C. overnight or at 37° C. for about 2 hr. The plates are washed three times and blocked with innocuous protein for about two hr followed by three washes. The sera obtained from the Xenomouse™ animals are added to the wells in serial dilution, and allowed to adsorb to the antigen for approximately 2 hr at room temperature, and washed three times. Positive and negative control wells are also prepared. After washing off excess unbound serum, bound antibody having human characteristics is detected by adding excess anti-human kappa, anti-human mu or anti-human gamma chain antibody conjugated to horse radish peroxidase (HRP) and allowing binding to proceed for approximately 1 hr. Chromogenic substrate for HRP is then added and the plates are read to determine the amount of bound HRP present in each well.

It is expected that the assay will show the production of both IgG and IgM, at titers in the range 1:3000 to 1:70000.

Equivalents

From the foregoing detailed description of the specific embodiments of the invention, it should be apparent that unique nucleotides, polypeptides, and methods of use thereof for the Wnt-7B-like genes have been described. Although particular embodiments have been disclosed herein in detail, this has been done by way of example for purposes of illustration only, and is not intended to be limiting with respectto the scope of the appended claims which follow. In particular, it is contemplated by the inventor that various substitutions, alterations, and modifications may be made to the invention without departing from the spirit and scope of the invention as defined by the claims. For instance, the choice of which Wnt-7B-like nucleotide or polypeptide or method of use thereof is believed to be a matter of routine for a person of ordinary skill in the art with knowledge of the embodiments described herein.

---

What is claimed is:

1. An isolated polypeptide comprising the amino acid sequence of SEQ ID NO:2.

2. An isolated polypeptide consisting of the amino acid sequence of SEQ ID NO:2.

* * * * *

SEQUENCE LISTING

```
<160> NUMBER OF SEQ ID NOS: 6

<210> SEQ ID NO 1
<211> LENGTH: 1070
<212> TYPE: DNA
<213> ORGANISM: Homo sapiens
<220> FEATURE:
<221> NAME/KEY: CDS
<222> LOCATION: (1)..(1047)

<400> SEQUENCE: 1 atg cac aga aac ttt cgc aag tgg att ttc tac gtg ttt ctc tgc ttt      48
Met His Arg Asn Phe Arg Lys Trp Ile Phe Tyr Val Phe Leu Cys Phe
  1               5                  10                  15 ggc gtc ctg tac gtg aag ctc gga gca ctg tca tcc gtg gtg gcc ctg      96
Gly Val Leu Tyr Val Lys Leu Gly Ala Leu Ser Ser Val Val Ala Leu
             20                  25                  30 gga gcc aac atc atc tgc aac aag att cct ggc cta gcc ccg cgg cag     144
Gly Ala Asn Ile Ile Cys Asn Lys Ile Pro Gly Leu Ala Pro Arg Gln
         35                  40                  45 cgt gcc atc tgc cag agt cgg ccc gat gcc atc att gtg att ggg gag     192
Arg Ala Ile Cys Gln Ser Arg Pro Asp Ala Ile Ile Val Ile Gly Glu
     50                  55                  60 ggg gcg cag atg ggc atc aac gag tgc cag tac cag ttc cgc ttc gga     240
Gly Ala Gln Met Gly Ile Asn Glu Cys Gln Tyr Gln Phe Arg Phe Gly
 65                  70                  75                  80 cgc tgg aac tgc tct gcc ctc ggc gag aag acc gtc ttc ggg caa gag     288
Arg Trp Asn Cys Ser Ala Leu Gly Glu Lys Thr Val Phe Gly Gln Glu
                 85                  90                  95
```

-continued

| | |
|---|---|
| ctc cga gta ggg agc cgt gag gct gcc ttc acg tac gcc atc acc gcg<br>Leu Arg Val Gly Ser Arg Glu Ala Ala Phe Thr Tyr Ala Ile Thr Ala<br>          100                          105                        110 | 336 |
| gct ggc gtg gcg cac gcc gtc acc gct gcc tgc agc caa ggg aac ctg<br>Ala Gly Val Ala His Ala Val Thr Ala Ala Cys Ser Gln Gly Asn Leu<br>115                       120                     125 | 384 |
| agc aac tgc ggc tgc gac cgc gag aag cag ggc tac tac aac caa gcc<br>Ser Asn Cys Gly Cys Asp Arg Glu Lys Gln Gly Tyr Tyr Asn Gln Ala<br>130                    135                     140 | 432 |
| gag ggc tgg aag tgg ggc ggc tgc tcg gcc gac gtg cgt tac ggc atc<br>Glu Gly Trp Lys Trp Gly Gly Cys Ser Ala Asp Val Arg Tyr Gly Ile<br>145                    150                   155                   160 | 480 |
| gac ttc tcc cgg cgc ttc gtg gac gct cgg gag atc aag aag aac gcg<br>Asp Phe Ser Arg Arg Phe Val Asp Ala Arg Glu Ile Lys Lys Asn Ala<br>                       165                     170                     175 | 528 |
| cgg cgc ctc atg aac ctg cat aac aat gag gcc ggc agg aag gtt cta<br>Arg Arg Leu Met Asn Leu His Asn Asn Glu Ala Gly Arg Lys Val Leu<br>                180                     185                     190 | 576 |
| gag gac cgg atg cag ctg gag tgc aag tgc cac ggc gtg tct ggc tcc<br>Glu Asp Arg Met Gln Leu Glu Cys Lys Cys His Gly Val Ser Gly Ser<br>195                     200                     205 | 624 |
| tgc acc acc aaa acc tgc tgg acc acg ctg ccc aag ttc cga gag gtg<br>Cys Thr Thr Lys Thr Cys Trp Thr Thr Leu Pro Lys Phe Arg Glu Val<br>210                       215                     220 | 672 |
| ggc cac ctg ctg aag gag aag tac aac gcg gcc gtg cag gtg gag gtg<br>Gly His Leu Leu Lys Glu Lys Tyr Asn Ala Ala Val Gln Val Glu Val<br>225                     230                     235                   240 | 720 |
| gtg cgg gcc agc cgt ctg cgg cag ccc acc ttc ctg cgc atc aaa cag<br>Val Arg Ala Ser Arg Leu Arg Gln Pro Thr Phe Leu Arg Ile Lys Gln<br>                       245                     250                     255 | 768 |
| ctg cgc agc tat cag aag ccc atg gag aca gac ctg gtg tac att gag<br>Leu Arg Ser Tyr Gln Lys Pro Met Glu Thr Asp Leu Val Tyr Ile Glu<br>260                     265                     270 | 816 |
| aag tcg ccc aac tac tgc gag gag gac gcg gcc acg ggc agc gtg ggc<br>Lys Ser Pro Asn Tyr Cys Glu Glu Asp Ala Ala Thr Gly Ser Val Gly<br>275                     280                     285 | 864 |
| acg cag ggc cgt ctc tgc aac cgc acg tcg ccc ggc gcg gac gac tgt<br>Thr Gln Gly Arg Leu Cys Asn Arg Thr Ser Pro Gly Ala Asp Asp Cys<br>290                     295                     300 | 912 |
| gac acc atg tgc tgc ggc cga ggc tac aac acc cac cag tac acc aag<br>Asp Thr Met Cys Cys Gly Arg Gly Tyr Asn Thr His Gln Tyr Thr Lys<br>305                     310                     315                   320 | 960 |
| gtg tgg cag tgc aac tgc aaa ttc cac tgg tgc tgc ttc gtc aag tgc<br>Val Trp Gln Cys Asn Cys Lys Phe His Trp Cys Cys Phe Val Lys Cys<br>                       325                     330                     335 | 1008 |
| aac acc tgc agc gag cgc acc gag gtc ttc acc tgc aag tgagccaggc<br>Asn Thr Cys Ser Glu Arg Thr Glu Val Phe Thr Cys Lys<br>340                     345 | 1057 |
| ccggaggcgg ccc | 1070 |

<210> SEQ ID NO 2
<211> LENGTH: 349
<212> TYPE: PRT
<213> ORGANISM: Homo sapiens

<400> SEQUENCE: 2

Met His Arg Asn Phe Arg Lys Trp Ile Phe Tyr Val Phe Leu Cys Phe
  1                5                    10                   15

Gly Val Leu Tyr Val Lys Leu Gly Ala Leu Ser Ser Val Val Ala Leu
                 20                    25                    30

```
Gly Ala Asn Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
     50                  55                  60

Gly Ala Gln Met Gly Ile Asn Glu Cys Gln Tyr Gln Phe Arg Phe Gly
 65                  70                  75                  80

Arg Trp Asn Cys Ser Ala Leu Gly Glu Lys Thr Val Phe Gly Gln Glu
                 85                  90                  95

Leu Arg Val Gly Ser Arg Glu Ala Ala Phe Thr Tyr Ala Ile Thr Ala
             100                 105                 110

Ala Gly Val Ala His Ala Val Thr Ala Ala Cys Ser Gln Gly Asn Leu
         115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Gln Leu Glu Cys Lys Cys His Gly Val Ser Gly Ser
        195                 200                 205

Cys Thr Thr Lys Thr Cys Trp Thr Thr Leu Pro Lys Phe Arg Glu Val
210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Asp Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345

<210> SEQ ID NO 3
<211> LENGTH: 349
<212> TYPE: PRT
<213> ORGANISM: Mus sp.

<400> SEQUENCE: 3

Met His Arg Asn Phe Arg Lys Trp Ile Phe Tyr Val Phe Leu Cys Phe
 1               5                  10                  15

Gly Val Leu Tyr Val Lys Leu Gly Ala Leu Ser Ser Val Val Ala Leu
             20                  25                  30

Gly Ala Asn Ile Ile Cys Asn Lys Ile Pro Gly Leu Ala Pro Arg Gln
            35                  40                  45

Arg Ala Ile Cys Gln Ser Arg Pro Asp Ala Ile Ile Val Ile Gly Glu
```

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |

Gly Ala Gln Met Gly Ile Asp Glu Cys Gln His Gln Phe Arg Phe Gly
65                  70                  75                  80

Arg Trp Asn Cys Ser Ala Leu Gly Glu Lys Thr Val Phe Gly Gln Glu
                85                  90                  95

Leu Arg Val Gly Ser Arg Glu Ala Ala Phe Thr Tyr Ala Ile Thr Ala
            100                 105                 110

Ala Gly Val Ala His Ala Val Thr Ala Ala Cys Ser Gln Gly Asn Leu
        115                 120                 125

Ser Asn Cys Gly Cys Asp Arg Glu Lys Gln Gly Tyr Tyr Asn Gln Ala
    130                 135                 140

Glu Gly Trp Lys Trp Gly Gly Cys Ser Ala Asp Val Arg Tyr Gly Ile
145                 150                 155                 160

Asp Phe Ser Arg Arg Phe Val Asp Ala Arg Glu Ile Lys Lys Asn Ala
                165                 170                 175

Arg Arg Leu Met Asn Leu His Asn Asn Glu Ala Gly Arg Lys Val Leu
            180                 185                 190

Glu Asp Arg Met Lys Leu Glu Cys Lys Cys His Gly Val Ser Gly Ser
        195                 200                 205

Cys Thr Thr Lys Thr Cys Trp Thr Thr Leu Pro Lys Phe Arg Glu Val
    210                 215                 220

Gly His Leu Leu Lys Glu Lys Tyr Asn Ala Ala Val Gln Val Glu Val
225                 230                 235                 240

Val Arg Ala Ser Arg Leu Arg Gln Pro Thr Phe Leu Arg Ile Lys Gln
                245                 250                 255

Leu Arg Ser Tyr Gln Lys Pro Met Glu Thr Asp Leu Val Tyr Ile Glu
            260                 265                 270

Lys Ser Pro Asn Tyr Cys Glu Glu Asp Ala Ala Thr Gly Ser Val Gly
        275                 280                 285

Thr Gln Gly Arg Leu Cys Asn Arg Thr Ser Pro Gly Ala Asp Gly Cys
    290                 295                 300

Asp Thr Met Cys Cys Gly Arg Gly Tyr Asn Thr His Gln Tyr Thr Lys
305                 310                 315                 320

Val Trp Gln Cys Asn Cys Lys Phe His Trp Cys Cys Phe Val Lys Cys
                325                 330                 335

Asn Thr Cys Ser Glu Arg Thr Glu Val Phe Thr Cys Lys
            340                 345

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: SYNTHETIC
      PCR PRIMER

<400> SEQUENCE: 4
ccggcctcat tgttatgca                                                    19

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:  SYNTHETIC
      PCR PRIMER

<400> SEQUENCE: 5

```
tctcccggcg cttcg                                                      15

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      TAQMAN PROBE

<400> SEQUENCE: 6
cgcgcgttct tcttgatctc ccg                                             23
```